US008076374B2

(12) United States Patent
Chappell et al.

(10) Patent No.: US 8,076,374 B2
(45) Date of Patent: Dec. 13, 2011

(54) GLUCAGON RECEPTOR ANTAGONISTS, PREPARATION AND THERAPEUTIC USES

(75) Inventors: Mark Donald Chappell, Noblesville, IN (US); Scott Eugene Conner, Indianapolis, IN (US); Philip Arthur Hipskind, New Palestine, IN (US); Jason Eric Lamar, Indianapolis, IN (US); Guoxin Zhu, Shanghai (CN)

(73) Assignee: Eli Lilly and Company, Indianapolis, IN (US)

( * ) Notice: Subject to any disclaimer, the term of this patent is extended or adjusted under 35 U.S.C. 154(b) by 663 days.

(21) Appl. No.: 12/093,598

(22) PCT Filed: Nov. 10, 2006

(86) PCT No.: PCT/US2006/060769
§ 371 (c)(1),
(2), (4) Date: May 14, 2008

(87) PCT Pub. No.: WO2007/114855
PCT Pub. Date: Oct. 11, 2007

(65) Prior Publication Data
US 2008/0319074 A1 Dec. 25, 2008

Related U.S. Application Data

(60) Provisional application No. 60/737,979, filed on Nov. 18, 2005.

(51) Int. Cl.
*A61K 31/195* (2006.01)
*C07C 229/22* (2006.01)
*A61P 3/10* (2006.01)

(52) U.S. Cl. ...................... 514/563; 562/450

(58) Field of Classification Search ........................ None
See application file for complete search history.

(56) References Cited

U.S. PATENT DOCUMENTS 5,811,459 A 9/1998 Breault et al.

FOREIGN PATENT DOCUMENTS

| WO | WO 03/048109 | | 6/2003 |
| WO | WO 2004/002480 | | 1/2004 |
| WO | WO 2004/056763 | A | 7/2004 |
| WO | WO2004/063147 | * | 7/2004 |
| WO | WO 2005/102067 | A | 9/2006 |

OTHER PUBLICATIONS

Kurukulasuriya et al.; Biaryl amide glucagon receptor antagonists, *Bioorganic & Medicinal Chemistry Letters*, vol. 14, No. 9, pp. 2047-2050 (2004).
Beasley, Helen L. et al., "Development of a Panel of Immunoassays for Monitory DDT, Its Metabolites, and Analogs in Food and Environmental Matrixes", *Journal of Agricultural and Food Chemistry*, 46(8), pp. 3339-3352; compound Hapten VI, 1998.
Kundu, B et al., "Identification of novel alpha-glucosidase inhibitors by screening libraries based on N-'r-(Benzyloxy) benzoyl! Alanine derivatives", *Chemical Abstracts Service*, 5(7), pp. 545-550, 2002.

* cited by examiner

*Primary Examiner* — Barbara P Badio
*Assistant Examiner* — Sara E Townsley
(74) *Attorney, Agent, or Firm* — Dan L. Wood

(57) ABSTRACT

The present invention discloses novel compounds of Formula (I), or pharmaceutically acceptable salts thereof, which have glucagon receptor antagonist or inverse agonist activity, as well as methods for preparing such compounds. In another embodiment, the invention discloses pharmaceutical compositions comprising compounds of Formula (I) as well as methods of using them to treat diabetic and other glucagon related metabolic disorders, and the like.

10 Claims, No Drawings

GLUCAGON RECEPTOR ANTAGONISTS, PREPARATION AND THERAPEUTIC USES

This is the national phase application, under 35 USC 371, for PCT/US2006/060769, filed Nov. 10, 2006, which claims the benefit, under 35 USC 119(e), of US provisional application 60/737,979 filed Nov. 18, 2005.

This invention relates to compounds that are antagonists or inverse agonists of the glucagon receptor, and to pharmaceutical compositions thereof, and the uses of these compounds and compositions in the treatment of the human or animal body. The present compounds show a high affinity and selective binding for the glucagon receptor, and as such are useful in the treatment of disorders responsive to the modulation of glucagon receptors, such as diabetic and other glucagon related metabolic disorders, and the like.

Glucagon is a key hormonal agent that, in cooperation with insulin, mediates homeostatic regulation of the amount of glucose in the blood. Glucagon primarily acts by stimulating certain cells (important among these are liver cells) to release glucose when blood glucose levels fall. The action of glucagon is opposite to that of insulin, which stimulates cells to take up and store glucose whenever blood glucose levels rise. Both glucagon and insulin are peptide hormones. Glucagon is produced in the alpha islet cells of the pancreas and insulin is produced in the beta islet cells. Glucagon exerts its action by binding to and activating its receptor, which is a member of the Glucagon-Secretin branch of the 7-transmembrane G-protein coupled receptor family. The receptor functions by activating the adenylyl cyclase second messenger system resulting in an increase in cAMP levels. The glucagon receptor, or naturally occurring variants of the receptor, may possess intrinsic constitutive activity, in vitro, as well as in vivo (i.e. activity in the absence of an agonist). Compounds acting as inverse agonists can inhibit this activity. Diabetes mellitus is a common disorder of glucose metabolism. The disease is characterized by hyperglycemia and may be classified as type 1 diabetes, the insulin-dependent form, or type 2 diabetes, which is non-insulin-dependent in character. Subjects with type 1 diabetes are hyperglycemic and hypoinsulinemic, and the conventional treatment for this form of the disease is to provide insulin. However, in some patients with type 1 or type 2 diabetes, absolute or relative elevated glucagon levels have been shown to contribute to the hyperglycemic state. Both in healthy control animals as well as in animal models of type 1 and type 2 diabetes, removal of circulating glucagon with selective and specific antibodies has resulted in reduction of the glycemic level. Mice with a homozygous deletion of the glucagon receptor exhibit increased glucose tolerance. Also, inhibition of glucagon receptor expression using antisense oligonucleotides ameliorates diabetic syndrome in db/db mice. These studies suggest that glucagon suppression or an action that antagonizes glucagon could be a useful adjunct to conventional treatment of hyperglycemia in diabetic patients. The action of glucagon can be suppressed by providing an antagonist or an inverse agonist, i.e. substances that inhibit or prevent constituitive, or glucagon-induced, glucagon receptor mediated responses.

Several publications disclose peptides that are stated to act as glucagon antagonists. Peptide antagonists of peptide hormones are often potent; however they are generally known not to be orally available because of degradation by physiological enzymes and poor distribution in vivo. Therefore, orally available non-peptide antagonists of peptide hormones are generally preferred.

A number of publications have appeared in recent years reporting non-peptide agents that act at the glucagon receptor. For example, WO 03/048109, WO 2004/002480, and Kurukulasuriya et al., "Biaryl amide glucagon receptor antagonists" *Bioorganic & Medicinal Chemistry Letters*, vol. 14, no. 9, pages 2047-2050, 2004, each disclose non-peptide compounds allegedly having glucagon receptor antagonist activity. In spite of the number of treatments for diseases that involve glucagon, the current therapies suffer from one or more inadequacies, including poor or incomplete efficacy, unacceptable side effects, and contraindications for certain patient populations. Thus, there remains a need for an improved treatment using alternative or improved pharmaceutical agents that modulate glucagon receptor activity and treat the diseases that could benefit from glucagon receptor modulation. The present invention provides such a contribution to the art based on the finding that a novel class of compounds has a high affinity, selective, and potent inhibitory activity at the glucagon receptor. The present invention is distinct in the particular structures and their activities.

SUMMARY OF THE INVENTION

The present invention provides a compound structurally represented by Formula I:

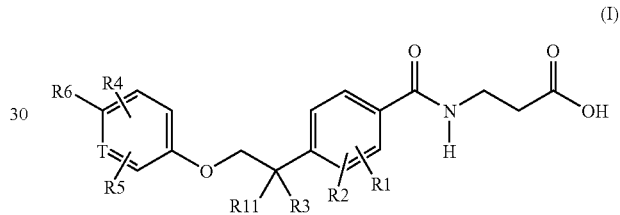

or a pharmaceutically acceptable salt thereof wherein:

T is independently carbon (substituted with hydrogen or the optional substituents as indicated herein), or nitrogen;

R1 and R2 are independently —H or -halogen;

R3 is
—($C_1$-$C_8$) alkyl(optionally substituted with 1 to 3 halogens),
—($C_2$-$C_7$)alkenyl(optionally substituted with 1 to 3 halogens); —($C_3$-$C_7$)cycloalkyl,
—($C_1$-$C_6$)alkyl-($C_3$-$C_7$)cycloalkyl, or —($C_3$-$C_7$)cycloalkyl-($C_1$-$C_6$)alkyl(optionally substituted with 1 to 3 halogens);

R4 and R5 are independently
—H, -halogen, -hydroxy, hydroxymethyl, —CN, —($C_1$-$C_7$)alkoxy, —($C_2$-$C_7$)alkenyl, or
—($C_1$-$C_6$)alkyl (optionally substituted with 1 to 3 halogens);

R6 is

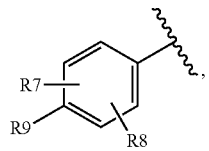

wherein the zig-zag mark shows the point of attachment to the parent molecule;

R7 and R8 are independently
—H, -halogen, —($C_1$-$C_6$)alkyl(optionally substituted with 1 to 3 halogens), —(C$_1$-C$_6$)alkoxy, —(C$_3$-C$_7$)cycloalkyl, —C(O)R10, —COOR10, —OC(O)R10,
—OS(O)$_2$R10, —SR10, —S(O)R10, —S(O)$_2$R10, or —O(C$_2$-C$_7$)alkenyl;

R9 is independently
—H, halogen, —CN, —(C$_3$-C$_7$)cycloalkyl, —C(O)R10, —COOR10, —OC(O)R10,
—OS(O)$_2$R10, —SR10, —S(O)R10, —S(O)$_2$R10, or —O(C$_2$-C$_7$)alkenyl,
(C$_1$-C$_3$)alkoxy(optionally substituted with 1 to 3 halogens), or —(C$_1$-C$_6$) alkyl (optionally substituted with 1 to 3 halogens);

R10 is independently at each occurrence
hydrogen, or —(C$_1$-C$_6$)alkyl(optionally substituted with 1 to 3 halogens); and R11 is independently
—H, —(C$_1$-C$_8$)alkyl(optionally substituted with 1 to 3 halogens), or
—(C$_2$-C$_7$)alkenyl(optionally substituted with 1 to 3 halogens); provided however that if R11 is —(C$_1$-C$_8$)alkyl (optionally substituted with 1 to 3 halogens), or
—(C$_2$-C$_7$)alkenyl(optionally substituted with 1 to 3 halogens) then R3 is the same moiety as R11;
or R11 and R3 together with the carbon to which they are attached form a cycloalkyl ring having five carbons (wherein optionally the cycloalkyl ring having five carbons may contain one double bond).

The present invention provides compounds that are useful as glucagon receptor antagonists or inverse agonists. The present invention further provides compounds that are selective antagonists or inverse agonists of the glucagon receptor over the GLP-1 receptor. The present invention further provides a pharmaceutical composition which comprises a compound of Formula I, or a pharmaceutical salt thereof, and a pharmaceutically acceptable carrier, diluent, or excipient. The present invention further provides methods of using these compounds and compositions in the treatment of disorders responsive to the modulation of glucagon receptors, such as diabetic and other glucagon related metabolic disorders.

DETAILED DESCRIPTION OF THE INVENTION

In one embodiment, the present invention provides compounds of Formula I as described in detail herein. While all of the compounds of the present invention are useful, certain of the compounds are particularly interesting and are preferred. The following listing sets out several groups of preferred compounds. It will be understood that each of the listings may be combined with other listings to create additional groups of preferred embodiments as indicated herein.

In another embodiment the invention provides a compound of formula I wherein T is independently carbon (substituted with hydrogen or the optional substituents as indicated herein), or nitrogen;
R1 and R2 are —H;
R3 is
—(C$_1$-C$_8$)alkyl(optionally substituted with 1 to 3 halogens),
—(C$_2$-C$_7$)alkenyl(optionally substituted with 1 to 3 halogens); —(C$_3$-C$_6$)cycloalkyl,
—(C$_1$-C$_6$)alkyl-(C$_3$-C$_6$)cycloalkyl, or —(C$_3$-C$_6$)cycloalkyl-(C$_1$-C$_6$)alkyl(optionally substituted with 1 to 3 halogens);
R4 and R5 are independently
—H, -halogen, or —(C$_1$-C$_6$)alkyl (optionally substituted with 1 to 3 halogens);

R6 is

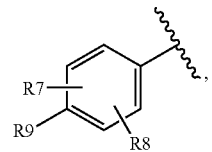

wherein the zig-zag mark shows the point of attachment to the parent molecule;
R7 and R8 are independently
—H, -halogen, —(C$_1$-C$_3$)alkyl(optionally substituted with 1 to 3 halogens), —(C$_1$-C$_3$)alkoxy;
R9 is independently
—H, halogen, or —(C$_1$-C$_6$)alkyl (optionally substituted with 1 to 3 halogens); and
R11 is independently
—H, —(C$_1$-C$_8$)alkyl(optionally substituted with 1 to 3 halogens), or
—(C$_2$-C$_7$)alkenyl(optionally substituted with 1 to 3 halogens); provided however that if R11 is —(C$_1$-C$_8$)alkyl (optionally substituted with 1 to 3 halogens), or
—(C$_2$-C$_7$)alkenyl(optionally substituted with 1 to 3 halogens) then R3 is the same moiety as R11;
or R11 and R3 together with the carbon to which they are attached form a cycloalkyl ring having five carbons (wherein optionally the cycloalkyl ring having five carbons may contain one double bond).

In another embodiment the invention provides a compound of formula I wherein R1 and R2 are —H; T is carbon:
R3 is
—(C$_1$-C$_8$)alkyl(optionally substituted with 1 to 3 halogens),
—(C$_2$-C$_3$)alkenyl(optionally substituted with 1 to 3 halogens); —(C$_3$-C$_6$)cycloalkyl,
—(C$_1$-C$_6$)alkyl-(C$_3$-C$_6$)cycloalkyl, or —(C$_3$-C$_6$)cycloalkyl-(C$_1$-C$_6$)alkyl(optionally substituted with 1 to 3 halogens);
R4 and R5 are independently
—H, -halogen, or —CH$_3$ (optionally substituted with 1 to 3 halogens);

R6 is

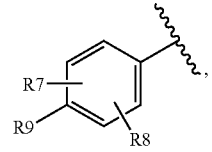

wherein the zig-zag mark shows the point of attachment to the parent molecule;
R7 and R8 are independently —H, or -halogen; and
R9 is independently —(C$_1$-C$_6$)alkyl (optionally substituted with 1 to 3 halogens); and
R11 is independently
—H, —(C$_1$-C$_8$)alkyl(optionally substituted with 1 to 3 halogens), or
—(C$_2$-C$_3$)alkenyl(optionally substituted with 1 to 3 halogens); provided however that if R11 is —(C$_2$-C$_3$)alkyl (optionally substituted with 1 to 3 halogens), or
—(C$_2$-C$_3$)alkenyl(optionally substituted with 1 to 3 halogens) then R3 is the same moiety as R1;

or R11 and R3 together with the carbon to which they are attached form a cycloalkyl ring having five carbons (wherein optionally the cycloalkyl ring having five carbons may contain one double bond).

In another embodiment the invention provides a compound of formula I wherein T is independently carbon (substituted with hydrogen or the optional substituents as indicated herein);
R1 and R2 are —H;
R3 is —($C_1$-$C_8$)alkyl(optionally substituted with 1 to 3 halogens), —($C_3$-$C_6$)cycloalkyl, —($C_1$-$C_6$)alkyl-($C_3$-$C_6$)cycloalkyl, or —($C_3$-$C_6$)cycloalkyl-($C_1$-$C_6$)alkyl(optionally substituted with 1 to 3 halogens); R4 and R5 are —$CH_3$ (optionally substituted with 1 to 3 halogens) and each occupies a position adjacent to R6 on the phenyl ring to which R6 is attached;
R6 is

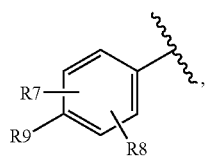

wherein the zig-zag mark shows the point of attachment to the parent molecule;
R7 and R8 are —H; and R9 is independently —($C_1$-$C_6$)alkyl (optionally substituted with 1 to 3 halogens); and R11 is —H.

In another embodiment the invention provides a compound of Formula I wherein R1 and R2 are independently hydrogen or halogen; R3 is methyl, ethyl, propyl, 2-propenyl, isopropyl, butyl, pentyl, hexyl, heptyl, octyl, 3,3-dimethylbutyl, 2-methylpropyl, 3-methyl-butyl, tertbutyl, 4-methylpentyl, 2,2-dimethylpropyl, 3-trifluoropropyl, 4-trifluorobutyl, cyclopropyl, cyclobutyl, cyclopentyl, or cyclohexyl; R4 and R5 are independently hydrogen, methyl, ethyl, tertbutyl, cyclohexyl, pentyl, isopropoxy, chloro, fluoro, bromo, hydroxy, trifluoromethyl, —CN, methoxy, hydroxymethyl, 4-methylpentyloxy, or pentyloxy; R7 and R8 are independently hydrogen, fluoro, chloro, methyl, ethyl, pentyl, isopropyl, tertbutyl, trifluoromethyl, acetyl, 2-methylpropyl, methoxy, cyclohexyl, or trifluoromethoxy; R9 is hydrogen, bromo, fluoro, methyl, tertbutyl, trifluoromethyl, or isopropyl; R11 is —H, methyl, ethyl, propyl, or 2-propenyl, (provided that when R11 is methyl, ethyl, propyl, or 2-propenyl, then R3 is the same moiety as R11), or R11 and R3 together with the carbon to which they are attached form cyclopentyl, or cyclopent-3-enyl.

Other embodiments of the invention are provided wherein each of the embodiments described herein above is further narrowed as described in the following preferences. Specifically, each of the preferences below is independently combined with each of the embodiments above, and the particular combination provides another embodiment in which the variable indicated in the preference is narrowed according to the preference.

Preferably T is nitrogen. Preferably T is carbon (substituted with hydrogen or the optional substituents as indicated herein). Preferably T is carbon (substituted with hydrogen).

Preferably R1 is —H. Preferably R1 is fluorine. Preferably R1 is chlorine. Preferably R2 is —H. Preferably R2 is fluorine. Preferably R2 is chlorine. Preferably R1 and R2 are —H. Preferably R1 is fluorine and R2 is fluorine.

Preferably R3 is —($C_1$-$C_8$)alkyl(optionally substituted with 1 to 3 halogens). Preferably R3 is ethyl, propyl, isopropyl, butyl, tertbutyl, 3-methyl-butyl, pentyl, hexyl, heptyl, octyl, 3,3-dimethylbutyl, 2-methylpropyl, 4-methylpentyl, 2,2-dimethylpropyl, 3,3,3-trifluoropropyl, or 4-trifluorbutyl. Preferably R3 is isopropyl, butyl, tertbutyl, 3-methyl-butyl, pentyl, 3,3-dimethylbutyl, 2-methylpropyl, 4-methylpentyl, 2,2-dimethylpropyl, 3,3,3-trifluoropropyl, or 4,4,4-trifluorobutyl. Preferably R3 is isopropyl, 3-methyl-butyl, trifluoropropyl, or 4,4,4-trifluorobutyl.

Preferably R3 is —($C_2$-$C_7$)alkenyl. Preferably $R_3$ is —($C_2$-$C_3$)alkenyl. Preferably R3 is 2-propenyl. Preferably $R_3$ is —($C_3$-$C_7$)cycloalkyl. Preferably R3 is cyclopropyl, cyclobutyl, cyclopentyl, or cyclohexyl. Preferably R3 is cyclopropyl. Preferably R3 is cyclobutyl. Preferably R3 is cyclopentyl. Preferably R3 is cyclohexyl.

Preferably R3 is —($C_1$-$C_6$)alkyl-($C_3$-$C_7$)cycloalkyl. Preferably R3 is —($C_1$-$C_3$)alkyl-($C_3$-$C_6$)cycloalkyl. Preferably R3 is —($C_1$-$C_3$)alkyl-cyclopropyl. Preferably R3 is —($C_1$-$C_3$)alkyl-cyclobutyl. Preferably R3 is —($C_1$-$C_3$)alkyl-cyclopentyl. Preferably R3 is —($C_1$-$C_3$)alkyl-cyclohexyl.

Preferably R3 is —($C_3$-$C_7$)cycloalkyl-($C_1$-$C_6$)alkyl(optionally substituted with 1 to 3 halogens). Preferably R3 is -cyclopropyl-($C_1$-$C_6$)alkyl(optionally substituted with 1 to 3 halogens). Preferably R3 is -cyclobutyl-($C_1$-$C_6$)alkyl(optionally substituted with 1 to 3 halogens). Preferably R3 is -cyclopentyl-($C_1$-$C_6$)alkyl(optionally substituted with 1 to 3 halogens). Preferably R3 is -cyclohexyl-($C_1$-$C_6$)alkyl(optionally substituted with 1 to 3 halogens).

Preferably R4 is —H, -halogen, -hydroxy, hydroxymethyl, or —($C_1$-$C_6$)alkyl (optionally substituted with 1 to 3 halogens). Preferably R4 is —H, -halogen, or —($C_1$-$C_3$)alkyl (optionally substituted with 1 to 3 halogens). Preferably R4 is —H, -halogen, or —$CH_3$. Preferably R4 is —H. Preferably R4 is fluorine, chlorine, or bromine. Preferably R4 is —$CH_3$.

Preferably R5 is —H, -halogen, -hydroxy, hydroxymethyl, or —($C_1$-$C_6$)alkyl (optionally substituted with 1 to 3 halogens). Preferably R5 is —H, -halogen, or —($C_1$-$C_3$)alkyl (optionally substituted with 1 to 3 halogens). Preferably R5 is —H, -halogen, or —$CH_3$. Preferably R5 is —H. Preferably R5 is fluorine, chlorine, or bromine. Preferably R5 is —$CH_3$.

Preferably R4 and R5 are —H. Preferably R4 is halogen and R5 is —H. Preferably R4 is —H and R5 is —$CH_3$. Preferably R4 and R5 are —$CH_3$. Preferably R4 and R5 are —$CH_3$ and each occupies a position adjacent to R6 on the phenyl ring to which R6 is attached.

Preferably R7 is -halogen, —($C_1$-$C_6$)alkyl(optionally substituted with 1 to 3 halogens), —($C_1$-$C_6$)alkoxy, —($C_3$-$C_7$)cycloalkyl, —C(O)R10, —COOR10, —OC(O)R10, —OS(O)$_2$R10, —SR10, —S(O)R10, —S(O)$_2$R10, or —O($C_2$-$C_7$)alkenyl. Preferably R7 is -halogen, —($C_1$-$C_6$)alkyl (optionally substituted with 1 to 3 halogens), or —($C_1$-$C_6$)alkoxy. Preferably R7 is —H or -halogen. Preferably R7 is —H.

Preferably R8 is -halogen, —($C_1$-$C_6$)alkyl(optionally substituted with 1 to 3 halogens), —($C_1$-$C_6$)alkoxy, —($C_3$-$C_7$)cycloalkyl, —C(O)R10, —COOR10, —OC(O)R10, —OS(O)$_2$R10, —SR10, —S(O)R10, —S(O)$_2$R10, or —O($C_2$-$C_7$)alkenyl. Preferably R8 is -halogen, —($C_1$-$C_6$)alkyl (optionally substituted with 1 to 3 halogens), or —($C_1$-$C_6$)alkoxy. Preferably R8 is —H or -halogen. Preferably R8 is —H. Preferably R7 is —H and R8 is —H.

Preferably R9 is —($C_1$-$C_6$)alkyl (optionally substituted with 1 to 3 halogens). Preferably R9 is methyl, ethyl, propyl, isopropyl, butyl, tertbutyl, trifluoromethyl, 3-methyl-butyl, pentyl, hexyl, 3,3-dimethylbutyl, 2-methylpropyl, 4-methylpentyl, 2,2-dimethylpropyl, 3-trifluoropropyl, or 4-trifluorobutyl. Preferably R9 is isopropyl, tertbutyl, or trifluoromethyl.

Preferably R7 is —H and R8 is —H, and R9 is isopropyl, tertbutyl, or trifluoromethyl.

Preferably R10 is independently at each occurrence —($C_1$-$C_6$)alkyl(optionally substituted with 1 to 3 halogens).

Preferably R11 is —H. Preferably R11 is —($C_1$-$C_8$)alkyl (optionally substituted with 1 to 3 halogens), or —($C_2$-$C_7$) alkenyl(optionally substituted with 1 to 3 halogens); provided however that if R11 is —($C_2$-$C_7$)alkyl(optionally substituted with 1 to 3 halogens), or —($C_1$-$C_8$)alkenyl(optionally substituted with 1 to 3 halogens), then R3 is the same moiety as R11. Preferably R11 and R3 together with the carbon to which they are attached form a cycloalkyl ring having five carbons (wherein optionally the cycloalkyl ring having five carbons may contain one double bond). Preferably R11 is —H, methyl, ethyl, propyl, or 2-propenyl, (provided that when R11 is methyl, ethyl, propyl, or 2-propenyl, then R3 is the same moiety as R11). Preferably R11 and R3 together with the carbon to which they are attached form cyclopentyl, or cyclopent-3-enyl.

Further embodiments of the invention include the compounds of formulae X1 to X22. A further embodiment of the invention are any novel intermediate preparations described herein which are useful for preparing the glucagon receptor antagonists or inverse agonists of formulae I, or X1 to X22.

TABLE 1

| Formula Number | Structure |
|---|---|
| X1 | 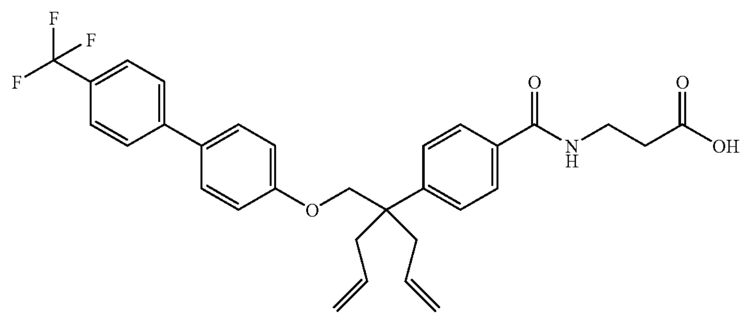 |
| X2 | 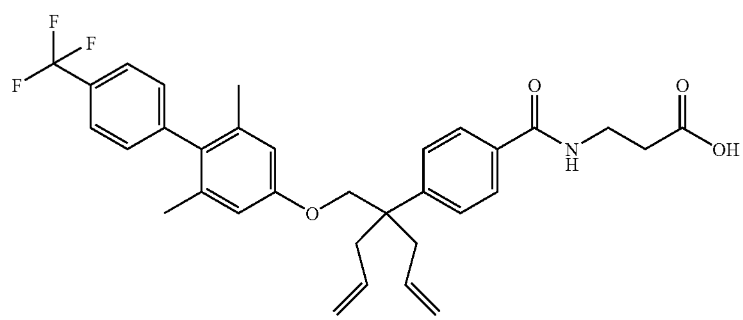 |
| X3 | 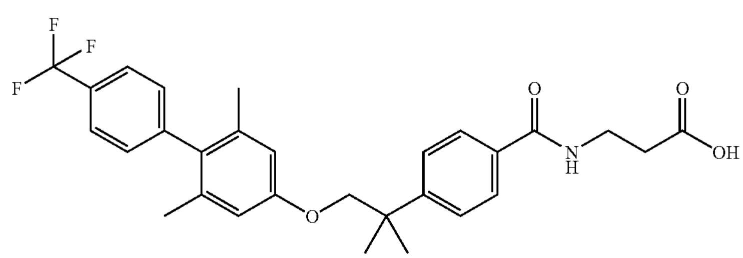 |
| X4 | 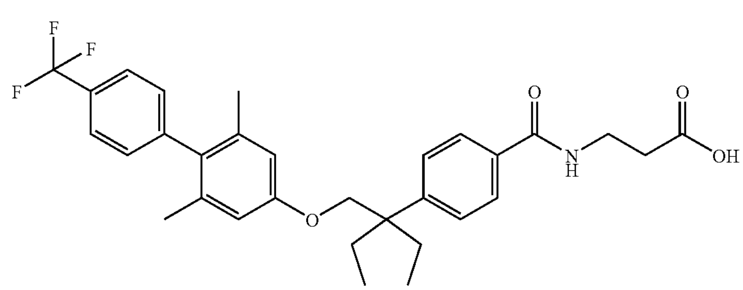 |

TABLE 1-continued
Formula Number | Structure
X5 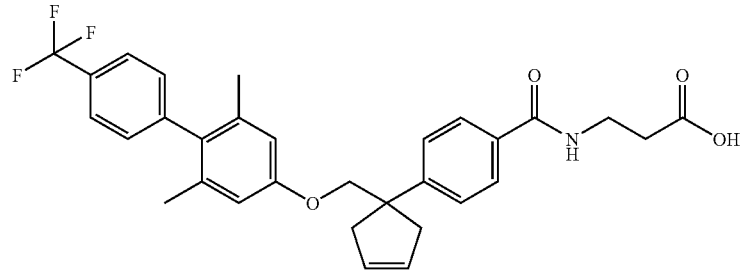
X6 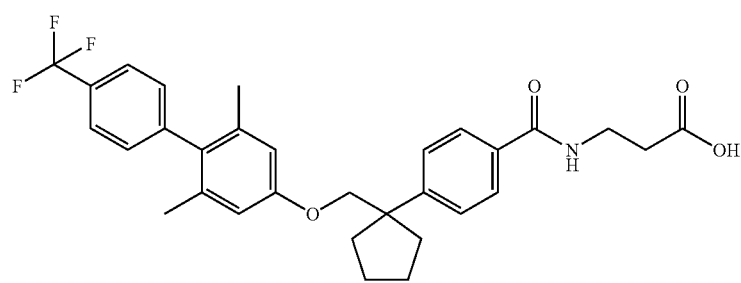
X7 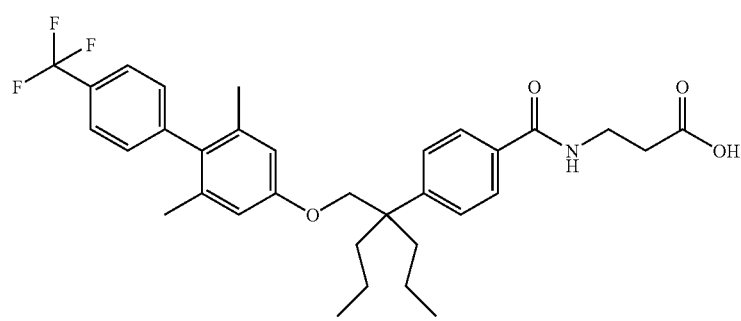
X8 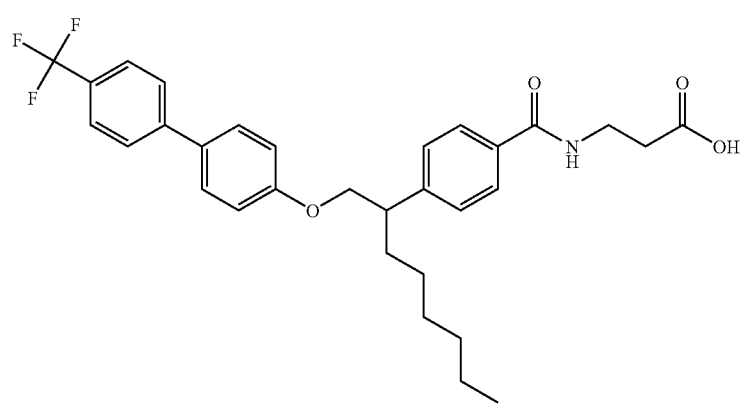

TABLE 1-continued
| Formula Number | Structure |
|---|---|
| X9 | 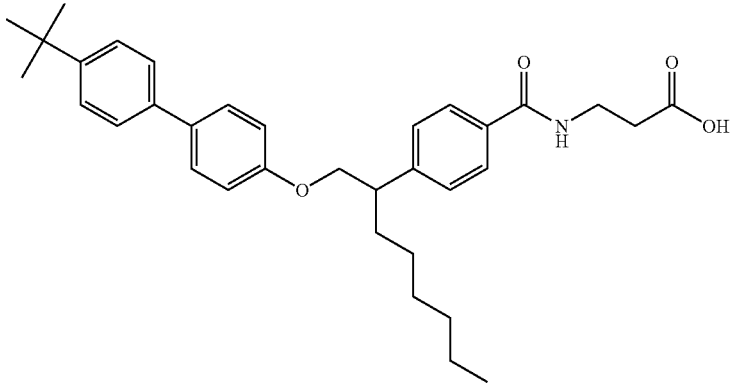 |
| X10 | 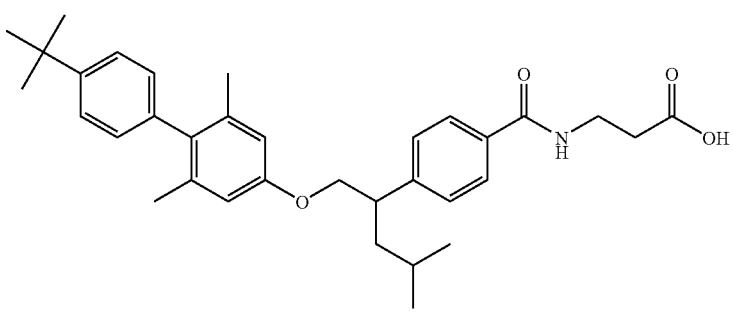 |
| X11 | 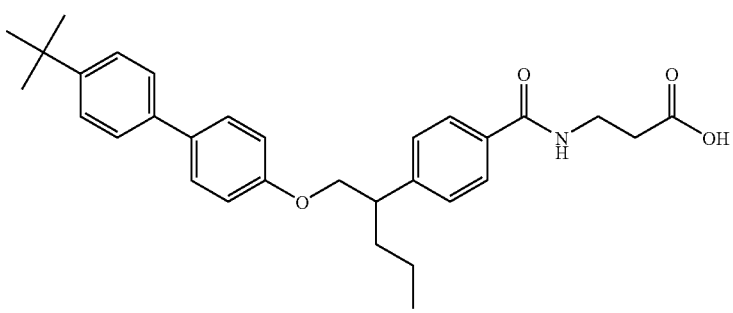 |
| X12 | 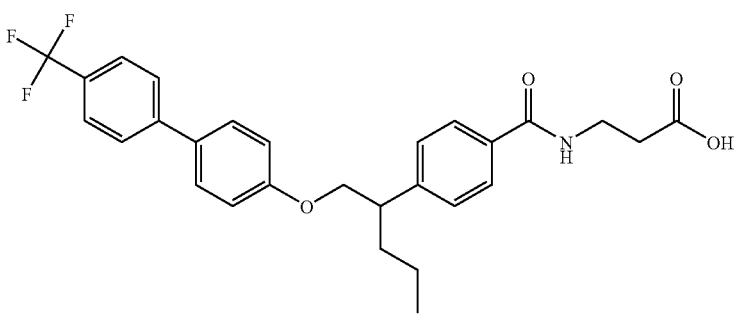 |

TABLE 1-continued
| Formula Number | Structure |
|---|---|
| X13 | 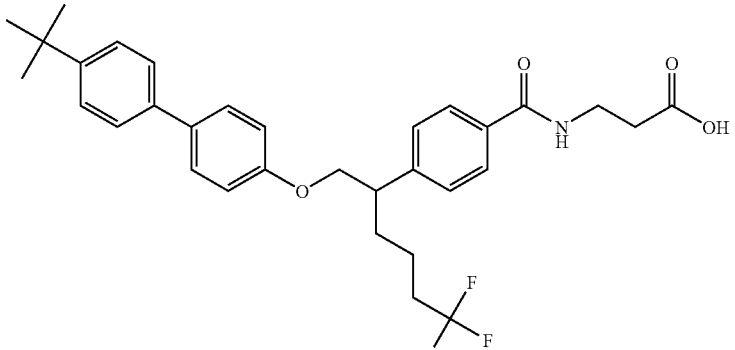 |
| X14 | 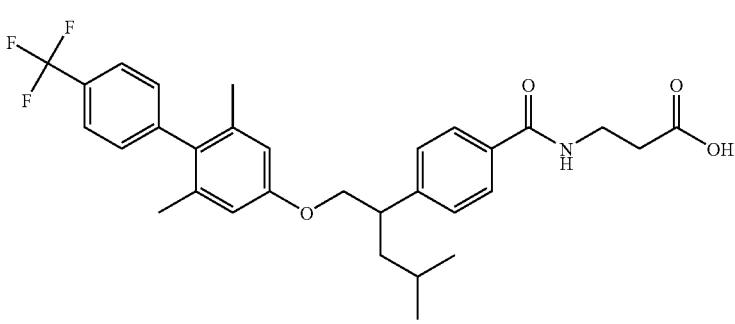 |
| X15 | 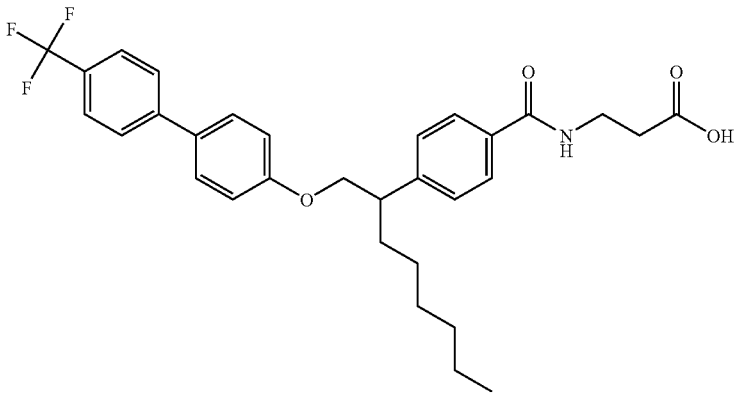 |
| X16 | 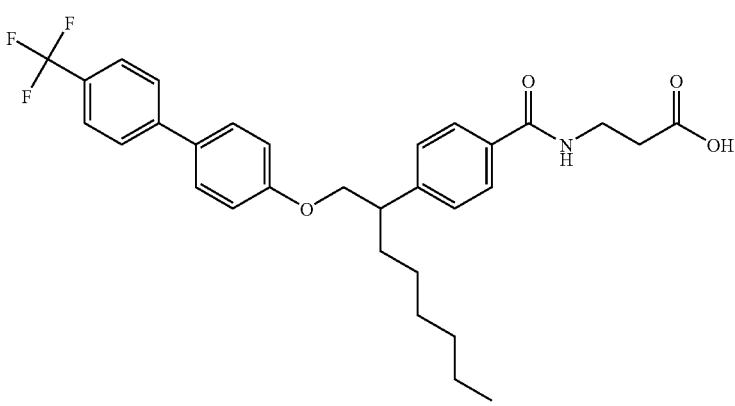 |

TABLE 1-continued

| Formula Number | Structure |
|---|---|
| X17 | 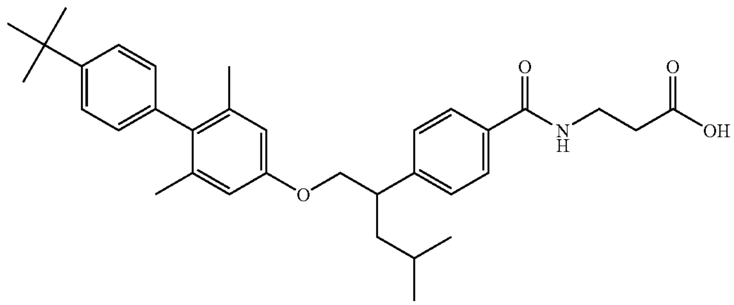 |
| X18 | 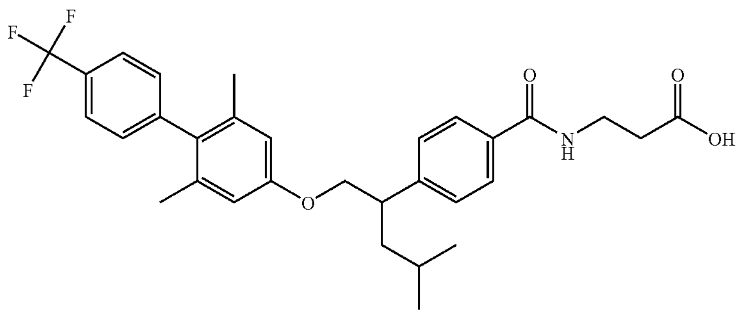 |
| X19 | 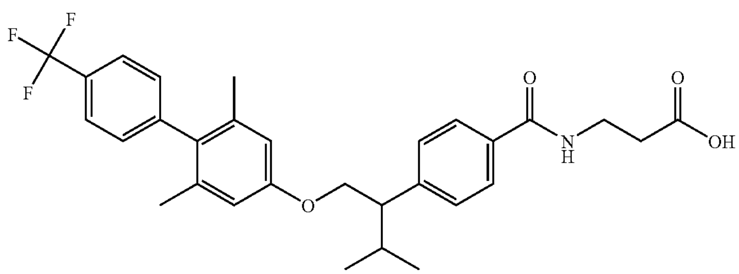 |
| X20 | 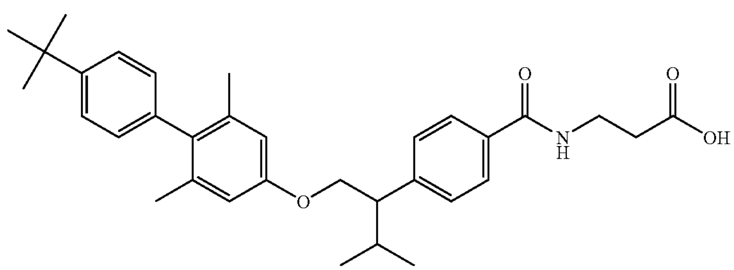 |
| X21 | 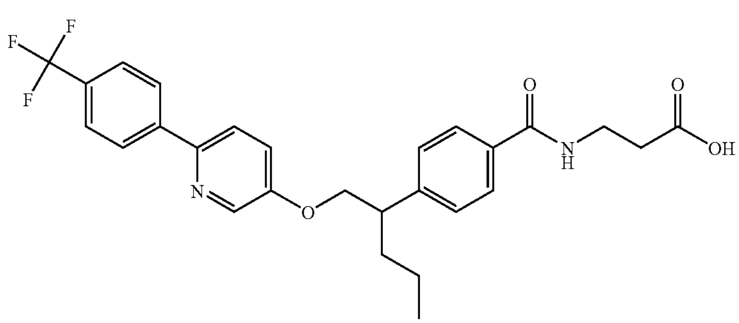 |

TABLE 1-continued

| Formula Number | Structure |
| --- | --- |
| X22 | (structure) |

Due to their interaction with the glucagon receptor, the present compounds are useful in the treatment of a wide range of conditions and disorders in which an interaction with the glucagon receptor is beneficial. These disorders and conditions are defined herein as "diabetic and other glucagon related metabolic disorders". One of skill in the art is able to identify "diabetic and other glucagon related metabolic disorders" by the involvement of glucagon receptor mediated signaling either in the pathophysiology of the disorder, or in the homeostatic response to the disorder. Thus, the compounds may find use for example to prevent, treat, or alleviate, diseases or conditions or associated symptoms or sequalae, of the endocrinological system, the central nervous system, the peripheral nervous system, the cardiovascular system, the pulmonary system, and the gastrointestinal system, while reducing and or eliminating one or more of the unwanted side effects associated with the current treatments. "Diabetic and other glucagon related metabolic disorders" include, but are not limited to, diabetes, type 1 diabetes, type 2 diabetes, hyperglycemia, hyper insulinemia, beta-cell rest, improved beta-cell function by restoring first phase response, prandial hyperglycemia, preventing apoptosis, impaired fasting glucose (IFG), metabolic syndrome, hypoglycemia, hyper-/hypokalemia, normalizing glucagon levels, improved LDL/HDL ratio, reducing snacking, eating disorders, weight loss, polycystic ovarian syndrome (PCOS), obesity as a consequence of diabetes, latent autoimmune diabetes in adults (LADA), insulitis, islet transplantation, pediatric diabetes, gestational diabetes, diabetic late complications, micro-/macroalbuminuria, nephropathy, retinopathy, neuropathy, diabetic foot ulcers, reduced intestinal motility due to glucagon administration, short bowel syndrome, antidiarrheic, increasing gastric secretion, decreased blood flow, erectile dysfunction, glaucoma, post surgical stress, ameliorating organ tissue injury caused by reperfusion of blood flow after ischemia, ischemic heart damage, heart insufficiency, congestive heart failure, stroke, myocardial infarction, arrhythmia, premature death, anti-apoptosis, wound healing, impaired glucose tolerance (IGT), insulin resistance syndromes, syndrome X, hyperlipidemia, dyslipidemia, hypertriglyceridemia, hyperlipoproteinemia, hypercholesterolemia, arteriosclerosis including atherosclerosis, glucagonomas, acute pancreatitis, cardiovascular diseases, hypertension, cardiac hypertrophy, gastrointestinal disorders, obesity, diabetes as a consequence of obesity, diabetic dyslipidemia, etc.

In addition, the present invention provides a compound of Formula I, or a pharmaceutical salt thereof, or a pharmaceutical composition which comprises a compound of Formula I, or a pharmaceutical salt thereof, and a pharmaceutically acceptable carrier, diluent, or excipient: for use in inhibiting the glucagon receptor; for use in inhibiting a glucagon receptor mediated cellular response in a mammal; for use in reducing the glycemic level in a mammal; for use in treating a disease arising from excessive glucagon; for use in treating diabetic and other glucagon related metabolic disorders in a mammal; and for use in treating diabetes, obesity, hyperglycemia, atherosclerosis, ischemic heart disease, stroke, neuropathy, and wound healing. Thus, the methods of this invention encompass a prophylactic and therapeutic administration of a compound of Formula I.

The present invention further provides the use of a compound of Formula I, or a pharmaceutical salt thereof for the manufacture of a medicament for inhibiting the glucagon receptor; for the manufacture of a medicament for inhibiting a glucagon receptor mediated cellular response in a mammal; for the manufacture of a medicament for reducing the glycemic level in a mammal; for the manufacture of a medicament for treating a disease arising from excessive glucagon; for the manufacture of a medicament for treating diabetic and other glucagon related metabolic disorders in a mammal; and for the manufacture of a medicament for preventing or treating diabetes, obesity, hyperglycemia, atherosclerosis, ischemic heart disease, stroke, neuropathy, and improper wound healing.

The present invention further provides a method of treating conditions resulting from excessive glucagon in a mammal; a method of inhibiting the glucagon receptor in a mammal; a method of inhibiting a glucagon receptor mediated cellular response in a mammal; a method of reducing the glycemic level in a mammal; a method of treating diabetic and other glucagon related metabolic disorders in a mammal; a method of preventing or treating diabetes, obesity, hyperglycemia, atherosclerosis, ischemic heart disease, stroke, neuropathy, and improper wound healing; said methods comprising administering to a mammal in need of such treatment a glucagon receptor-inhibiting amount of a compound of Formula I, or a pharmaceutically acceptable salt thereof, or a pharmaceutical composition which comprises a compound of Formula I, or a pharmaceutical salt thereof, and a pharmaceutically acceptable carrier, diluent, or excipient.

In addition, the present invention provides a pharmaceutical composition which comprises a compound of Formula I, or a pharmaceutical salt thereof, and a pharmaceutically acceptable carrier, diluent, or excipient: adapted for use in inhibiting the glucagon receptor; adapted for use in inhibiting glucagon receptor mediated cellular responses; adapted for use in reducing the glycemic level in a mammal; adapted for use in treating diabetic and other glucagon related metabolic disorders in a mammal; and adapted for use in preventing or treating diabetes, obesity, hyperglycemia, atherosclerosis, ischemic heart disease, stroke, neuropathy, and wound healing.

The compound or salt of the present invention further provides a diagnostic agent for identifying patients having a defect in the glucagon receptor, as a therapy to increase gastric acid secretions, and to reverse intestinal hypomobility due to glucagon administration. The invention also provides a method for the treatment of disorders or diseases, wherein a glucagon antagonistic action is beneficial, the method comprising administering to a subject in need thereof an effective amount of a compound according to the invention. In another embodiment of the invention, the present compounds are used for the preparation of a medicament for the treatment of any glucagon-mediated conditions and diseases. In another embodiment of the invention, the present compounds are used for the preparation of a medicament for the treatment of hyperglycemia. In yet another embodiment of the invention, the present compounds are used for the preparation of a medicament for lowering blood glucose in a mammal. The present compounds are effective in lowering the blood glucose, both in the fasting and the postprandial stage. In still another embodiment of the invention, the present compounds are used for the preparation of a pharmaceutical composition for the treatment of IGT. In a further embodiment of the invention, the present compounds are used for the preparation of a pharmaceutical composition for the treatment of type 2 diabetes. In yet a further embodiment of the invention the present compounds are used for the preparation of a pharmaceutical composition for the delaying or prevention of the progression from IGT to type 2 diabetes. In yet another embodiment of the invention the present compounds are used for the preparation of a pharmaceutical composition for the delaying or prevention of the progression from non-insulin requiring type 2 diabetes to insulin requiring type 2 diabetes. In a further embodiment of the invention the present compounds are used for the preparation of a pharmaceutical composition for the treatment of type 1 diabetes. Such treatment is normally accompanied by insulin therapy. In yet a further embodiment of the invention the present compounds are used for the preparation of a pharmaceutical composition for the treatment of obesity. In still a further embodiment of the invention the present compounds are used for the preparation of a pharmaceutical composition for the treatment of disorders of the lipid metabolism. In still another embodiment of the invention the present compounds are used for the preparation of a pharmaceutical composition for the treatment of an appetite regulation or energy expenditure disorder. In a further embodiment of the invention, treatment of a patient with the present compounds is combined with diet and/or exercise.

In a further aspect of the invention the present compounds are administered in combination with one or more further active substances in any suitable ratios. Such further active substances may for example be selected from antidiabetics, antiobesity agents, antihypertensive agents, agents for the treatment of complications resulting from or associated with diabetes and agents for the treatment of complications and disorders resulting from or associated with obesity. The following listing sets out several groups of combinations. It will be understood that each of the agents named may be combined with other agents named to create additional combinations.

Thus, in a further embodiment of the invention the present compounds may be administered in combination with one or more antidiabetics.

Suitable antidiabetic agents include insulin, insulin analogues and derivatives such as those disclosed in EP 792 290 (Novo Nordisk A/S), for example $N^{\epsilon B29}$-tetradecanoyl des (B30) human insulin, EP 214 826 and EP 705 275 (Novo Nordisk A/S), for example $ASP^{B28}$ human insulin, U.S. Pat. No. 5,504,188 (Eli Lilly), for example $Lys^{B28}$ $Pro^{B29}$ human insulin, EP 368 187 (Aventis), for example Lantus®, which are all incorporated herein by reference, GLP-1 and GLP-1 derivatives such as those disclosed in WO 98/08871 (Novo Nordisk A/S), which is incorporated herein by reference, as well as orally active hypoglycemic agents.

The orally active hypoglycemic agents preferably comprise imidazolines, sulphonylureas, biguanides, meglitinides, oxadiazolidinediones, thiazolidinediones, insulin sensitizers, insulin secretagogues, such as glimepiride, α-glucosidase inhibitors, agents acting on the ATP-dependent potassium channel of the β-cells for example potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), which are incorporated herein by reference, GLP-1 antagonists, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, activators of glucokinase (GK) such as those disclosed in WO 00/58293, WO 01/44216, WO 01/83465, WO 01/83478, WO 01/85706, WO 01/85707, and WO 02/08209 (Hoffman-La Roche) or those disclosed in WO 03/00262, WO 03/00267 and WO 03/15774 (AstraZeneca), which are incorporated herein by reference, GSK-3 (glycogen synthase kinase-3) inhibitors, compounds modifying the lipid metabolism such as antilipidemic agents such as HMG CoA inhibitors (statins), compounds lowering food intake, PPAR (Peroxisome proliferator-activated receptor) ligands including the PPAR-alpha, PPAR-gamma and PPAR-delta subtypes, and RXR (retinoid X receptor) agonists, such as ALRT-268, LG-1268 or LG-1069.

In another embodiment, the present compounds are administered in combination with insulin or an insulin analogue or derivative, such as $N^{\epsilon B29}$-tetradecanoyl des (B30) human insulin, $Asp^{B28}$ human insulin, $Lys^{B28}$ $Pro^{B29}$ human insulin, Lantus®, or a mix-preparation comprising one or more of these.

In a further embodiment of the invention the present compounds are administered in combination with a sulphonylurea such as glibenclamide, glipizide, tolbautamide, chloropamidem, tolazamide, glimepride, glicazide and glyburide.

In another embodiment of the invention the present compounds are administered in combination with a biguanide, for example, metformin.

In yet another embodiment of the invention the present compounds are administered in combination with a meglitinide, for example, repaglinide or nateglinide.

In still another embodiment of the invention the present compounds are administered in combination with a thiazolidinedione insulin sensitizer, for example, troglitazone, ciglitazone, piolitazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292 (Dr. Reddy's Research Foundation), which are incorporated herein by reference.

In still another embodiment of the invention the present compounds may be administered in combination with an insulin sensitizer, for example, such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 such as ragaglitazar (NN 622 or (−)DRF 2725) (Dr. Reddy's Research Foundation) and WO 00/23425, WO 00/23415, WO 00/23451, WO 00/23445, WO 00/23417, WO 00/23416, WO 00/63153, WO 63196, WO 00/63209, WO 00/63190 and WO 00/63189 (Novo Nordisk A/S), which are incorporated herein by reference.

In a further embodiment of the invention the present compounds are administered in combination with an α-glucosidase inhibitor, for example, voglibose, emiglitate, miglitol or acarbose.

In another embodiment of the invention the present compounds are administered in combination with an agent acting on the ATP-dependent potassium channel of the β-cells, for example, tolbutamide, glibenclamide, glipizide, glicazide, BTS-67582 or repaglinide.

In yet another embodiment of the invention the present compounds may be administered in combination with nateglinide.

In still another embodiment of the invention the present compounds are administered in combination with an antilipidemic agent or antihyperlipidemic agent for example cholestyramine, colestipol, clofibrate, gemfibrozil, lovastatin, pravastatin, simvastatin, pitavastatin, rosuvastatin, probucol, dextrothyroxine, fenofibrate or atorvastin.

In still another embodiment of the invention the present compounds are administered in combination with compounds lowering food intake.

In another embodiment of the invention, the present compounds are administered in combination with more than one of the above-mentioned compounds for example in combination with metformin and a sulphonylurea such as glyburide; a sulphonylurea and acarbose; nateglinide and metformin; repaglinide and metformin, acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

In a further embodiment of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140 MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, H3 histamine antagonists, opioid antagonists (such as naltrexone), exendin-4, GLP-1 and ciliary neurotrophic factor (such as axokine), cannaboid receptor antagonist for example CB-1 (such as rimonabant). In another embodiment the antiobesity agent is dexamphetamine or amphetamine. In another embodiment the antiobesity agent is leptin. In another embodiment the antiobesity agent is fenfluramine or exfenfluramine. In still another embodiment the antiobesity agent is sibutramine. In a further embodiment the antiobesity agent is orlistat. In another embodiment the antiobesity agent is mazindol or phentermine. In still another embodiment the antiobesity agent is phendimetrazine, diethylpropion, fluoxetine, bupropion, topiramate or ecopipam.

Furthermore, the present compounds may be administered in combination with one or more antihypertensive agents. Examples of antihypertensive agents are β-blockers such as alprenolol, atenolol, timolol, pindolol, propranolol and metoprolol, SCE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, $19^{th}$ Edition, Gennaro, Ed., Mack Publishing Co., Easton, Pa., 1995.

The compounds of the present invention may be administered in combination with FAS inhibitors.

The compounds of the present invention may also be administered in combination with chemical uncouplers, hormone sensitive lipase inhibitor, imidazolines, 11-β-hydroxysteroid dehydrogenase inhibitors, lipoprotein lipase activator, AMPK activators, immunosuppressive drugs, nicotinamide, ASIS, anti-androgens or carboxypeptidase inhibitors.

It should be understood that any suitable combination of the compounds according to the invention with diet and/or exercise, one or more of the above-mentioned compounds are considered to be within the scope of the present invention.

General terms used in the description of compounds, compositions, and methods herein described, bear their usual meanings. Throughout the instant application, the following terms have the indicated meanings:

"GLP-1" means glucagon-like peptide 1. The term "glucagon receptor" means one or more receptors that interact specifically with glucagon to result in a biological signal. The term "GLP-1 receptor" means one or more receptors that interact specifically with glucagon-like peptide 1 to result in a biological signal.

The term "glucagon receptor antagonist" means a compound of the present invention with the ability to block cAMP production in response glucagon. The term "glucagon receptor inverse agonist" means a compound of the present invention with the ability to inhibit the constitutive activity of glucagon receptor. The term "selective" antagonist or inverse agonist means a compound having greater affinity for the glucagon receptor as compared to the affinity for the GLP-1 receptor.

In the general formulae of the present document, the general chemical terms have their usual meanings. For example;

"Halogen" or "halo" means fluoro, chloro, bromo and iodo.

The term "alkyl," unless otherwise indicated, refers to those alkyl groups of a designated number of carbon atoms of either a straight or branched saturated configuration. As used herein, "($C_1$-$C_3$)alkyl" are one to three carbon atoms, such as methyl, ethyl, propyl, n-propyl, isopropyl, and the like and branched or isomeric forms thereof, and optionally may be substituted with one to three halogens or a designated number of substituents as set forth in the embodiments recited herein. "($C_1$-$C_6$)alkyl" are one to six carbon atoms such as methyl, ethyl, propyl, n-propyl, isopropyl, n-butyl, isobutyl, sec-butyl and tert-butyl, pentyl, isopentyl, hexyl, and the like, and branched or isomeric forms thereof, and optionally may be substituted with one to three halogens or a designated number of substituents as set forth in the embodiments recited herein. "($C_1$-$C_8$) alkyl" are one to eight carbon atoms, such as methyl, ethyl, propyl, butyl, pentyl, hexyl, heptyl, octyl, and the like, and branched or isomeric forms thereof, and optionally may be substituted with one to three halogens as set forth in the embodiments recited herein.

The term "($C_3$-$C_7$)cycloalkyl" refers to a saturated or partially saturated carbocycle containing one or more rings of from 3 to 7 carbon atoms. Examples of ($C_3$-$C_7$)cycloalkyl include but are not limited to cyclopropyl, cyclobutyl, cyclopentyl, cyclohexyl and cycloheptyl.

The term "($C_1$-$C_6$)alkoxy" represents an alkyl group of one to six carbon atoms attached through an oxygen bridge, such as methoxy, ethoxy, propoxy, isopropoxy, butoxy, tert-butoxy, pentoxy, and the like. The term "($C_1$-$C_7$)alkoxy" represents an alkyl group of one to seven carbon atoms attached through an oxygen bridge, such as methoxy, ethoxy, propoxy, isopropoxy, butoxy, tert-butoxy, pentoxy, and the like, and may be optionally substituted with three halogens as set forth in the embodiments recited herein.

The term "($C_2$-$C_7$)alkenyl" means hydrocarbon chain of two to seven carbon atoms of either a straight or branched configuration having at least one carbon-carbon double bond which may occur at any point along the chain, such as ethenyl, propenyl, butenyl, pentenyl, vinyl, alkyl, 2-butenyl and the like, and may be optionally substituted with one to three halogens as set forth in the embodiments recited herein. The term "($C_2$-$C_3$)alkenyl" means hydrocarbon chain of two or three carbon atoms of either a straight or branched configuration having at least one carbon-carbon double bond which may occur at any point along the chain, such as ethenyl, or propenyl.

The term "optionally substituted," or "optional substituents," as used herein, means that the groups in question are either unsubstituted or substituted with one or more of the substituents specified. When the groups in question are substituted with more than one substituent, the substituents may be the same or different. Furthermore, when using the terms "independently," "independently are," and "independently selected from" mean that the groups in question may be the same or different. Certain of the herein defined terms may occur more than once in the structural formulae, and upon such occurrence each term shall be defined independently of the other.

The term "patient" includes human and non-human animals such as companion animals (dogs and cats and the like) and livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. Yet other examples of livestock include fish, shellfish and crustaceans raised in aquaculture. Also included are exotic animals used in food production such as alligators, water buffalo and ratites (e.g., emu, rheas or ostriches). The patient to be treated is preferably a mammal, in particular a human being.

The term "a glucagon receptor mediated cellular response" includes various responses by mammalian cells to glucagon stimulation or glucagon receptor activity. For example "glucagon receptor mediated cellular responses," include but are not limited to, release of glucose from liver, or other cells, in response to glucagon stimulation or glucagon receptor activity. One of ordinary skill in the art can readily identify other cellular responses mediated by glucagon receptor activity, for example by observing a change in the responsive cellular endpoint after contacting the cell with an effective dose of glucagon.

The terms "treatment", "treating" and "treat", as used herein, include their generally accepted meanings, i.e., the management and care of a patient for the purpose of preventing, prohibiting, restraining, alleviating, ameliorating, slowing, stopping, delaying, or reversing the progression or severity of a disease, disorder, or pathological condition, described herein, including the alleviation or relief of symptoms or complications, or the cure or elimination of the disease, disorder, or condition.

"Composition" means a pharmaceutical composition and is intended to encompass a pharmaceutical product comprising the active ingredient(s) including compound(s) of Formula I, and the inert ingredient(s) that make up the carrier. Accordingly, the pharmaceutical compositions of the present invention encompass any composition made by admixing a compound of the present invention and a pharmaceutically acceptable carrier.

The term "suitable solvent" refers to any solvent, or mixture of solvents, inert to the ongoing reaction that sufficiently solubilizes the reactants to afford a medium within which to effect the desired reaction.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

The compounds of the present invention may be chiral, and it is intended that any enantiomers, whether pure, partially purified, or racemic mixtures, are included within the scope of the invention. Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention. Furthermore, some of the compounds of the present invention may exist in different tautomeric forms and it is intended that any tautomeric forms, which the compounds are able to form, are included within the scope of the present invention. The invention also includes tautomers, enantiomers and other stereoisomers of the compounds of Formula I. Such variations are contemplated to be within the scope of the invention.

The compounds of Formula I, when existing as a diastereomeric mixture, may be separated into diastereomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of Formula I may be obtained by stereospecific synthesis using optically pure starting materials or reagents of known configuration or through enantioselective synthesis.

The term "enantiomeric enrichment" as used herein refers to the increase in the amount of one enantiomer as compared to the other. A convenient method of expressing the enantiomeric enrichment achieved is the concept of enantiomeric excess, or "ee," which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of Formula I, can be prepared by one of ordinary skill in the art utilizing well known techniques and processes, such as those disclosed by J. Jacques, et al., "*Enantiomers, Racemates, and Resolutions*," John Wiley and Sons, Inc., 1981, and E. L. Eliel and S. H. Wilen," *Stereochemistry of Organic Compounds*," (Wiley-Interscience 1994), and European Patent Application No. EP-A-838448, published Apr. 29, 1998. Examples of resolutions include recrystallization techniques or chiral chromatography. Unless otherwise indicated, a compound indicated to be "isomer 1" will be the first isomer eluted from the chiral separation column and "isomer 2" will be the second.

In general, the term "pharmaceutical" when used as an adjective means substantially non-toxic to living organisms. For example, the term "pharmaceutical salt" as used herein, refers to salts of the compounds of Formula I, which are substantially non-toxic to living organisms. See, e.g., Berge, S. M, Bighley, L. D., and Monkhouse, D.C., "Pharmaceutical Salts," *J. Pharm. Sci.*, 66:1, 1977. The present invention also encompasses pharmaceutically acceptable salts of the present compounds, and common methodology for preparing them are well known in the art. See e.g., P. Stahl, et al., "Handbook Of Pharmaceutical Salts: Properties, Selection, and Use," (VCHA/Wiley-VCH, 2002); Berge, S. M, Bighley, L. D., and Monkhouse, D.C., "Pharmaceutical Salts," *J. Pharm. Sci.*, 66:1, 1977.

The invention also encompasses prodrugs of the present compounds, which on administration undergo chemical conversion by metabolic processes before becoming pharmacologically active substances. In general, such prodrugs will be functional derivatives of present compounds, which are readily convertible in vivo into a compound of the present invention. Conventional procedures for the selection and preparation of suitable prodrug derivatives are described, for example in "Design of Prodrugs", ed. H. Bundgaard, Elsevier, 1985.

The compounds of Formula I, can be prepared by one of ordinary skill in the art following a variety of procedures, some of which are illustrated in the procedures and schemes set forth below. The particular order of steps required to produce the compounds of Formula I is dependent upon the particular compound to being synthesized, the starting compound, and the relative liability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Schemes, Preparations, Examples and Procedures are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

The optimal time for performing the reactions of the Schemes, Preparations, Examples and Procedures can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formula I may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The terms and abbreviations used in the instant Schemes, Preparations, Examples and Procedures have their normal meanings unless otherwise designated. For example, as used herein, the following terms have the meanings indicated: "min" refers to minutes; "h" or "hr" refers to hours; "TLC" refers to thin layer chromatography; "HPLC" refers to high performance liquid chromatography; "Rf" refers to retention factor; "Rt" refers to retention time; "δ" refers to part per million down-field from tetramethylsilane; "MS" refers to mass spectrometry; "MS (ES)" refers to electron spray mass spectrometry, "UV" refers to ultraviolet spectrometry; "$^1$H NMR" refers to proton nuclear magnetic resonance spectrometry. In addition; "RT" refers to room temperature; "DEAD" refers to diethylazodicrboxylate; "PPh$_3$" refers to triphenylphosphine; "ADDP" refers to 1,1'-(azodicarbonyl) dipiperidine; "PBu$_3$" refers to tributylphosphine; "OTF" refers to triflate; "LAH" refers to lithium aluminum hydride; "DIBAL-H" refers to diisobutylaluminum hydride; "KOtBu" refers to potassoium t-butoxide; "THF" refers to tetrahydrofuran; "TBP" refers to tributylphosphine; "EDCI" refers to 1-(3-dimethylaminopropyl)-3-ethylcarbodiamide hydrochloride; "DMAP" refers to dimethylaminopyridine; "HNMe(OMe)" refers to N,N,dimethylhydroxyamine; "CDMT" refers to 2-chloro-4,6-dimethoxy-[1,3,5] triazine; "NMM" refers to N-methyl morpholine; "DCM" refers to dichloromethane; "DMSO" refers to dimethylsulfoxide; "ET₃N" refers to triethylamine; "DMF" refers to dimethylformamide; "Et" in a formula refers to ethyl, for example Et₂O refers to diethylether, and EtOAc refers to ethylacetate; "PyBOP" refers to bromo-tris-pyrrolidino-phosphonium hexafluorophosphate; "Me" refers to methyl as in MeOH which is methanol; "Pd/C" refers to 10% palladium on carbon. Unless otherwise indicated, isomer 1 refers to the first isomer to be eluted in a chiral separation and isomer 2 refers to the second isomer to be eluted in a chiral separation.

General Schemes

All of the compounds of the present invention can be chemically prepared, for example, by following the synthetic routes set forth in the Schemes and/or the Preparations and Examples below. However, the following discussion is not intended to be limiting to the scope of the present invention in any way. For example, the specific synthetic steps for each of the routes described may be combined in different ways, or in conjunction with steps from different schemes, to prepare additional compounds of Formula I.

Scheme I

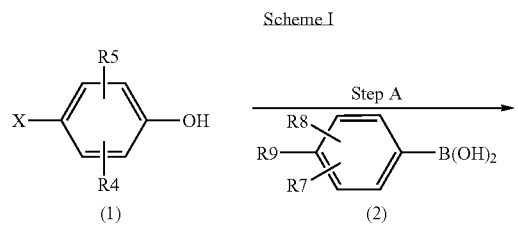

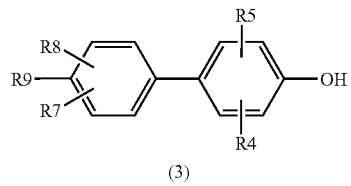

In Scheme I, Step A, a 4-halophenol of formula (1), (X=I or Br) is coupled with a phenyl boronic acid of formula (2), using a Suzuki reaction to provide the biphenyl hydroxy of formula (3). It will be recognized by one skilled in the art that such Suzuki couplings using aryl bromides and phenyl boronic acids can be effected using a wide variety of reaction conditions. Preferred conditions use oxydi-2,1-phenylene) bis(diphenylphosphine) in the presence of palladium (II) acetate and potassium fluoride, in an inert solvent, such as tetrahydrofuran. The reaction is heated at a temperature of 50° C. to the reflux temperature of the solvent for about 4 to 48 hours under nitrogen. The product can be purified by silica gel chromatography followed by recrystillization from isopropanol/heptane.

Another set of preferred conditions use tetrakis(triphenylphosphine)palladium with potassium fluoride under nitrogen. The reaction proceeds in an inert solvent such as toluene or benzene mixed with water, or toluene mixed with ethanol, at a temperature of 40° C. to the reflux temperature of the reaction for about 4 to 48 hours.

Yet another set of preferred conditions accomplishes the Suzuki coupling with palladium (II) acetate in the presence of potassium carbonate in water as the solvent. The reaction proceeds at 0 to 80° C. for 4 to 24 hours and is left open to the atmosphere.

Scheme II

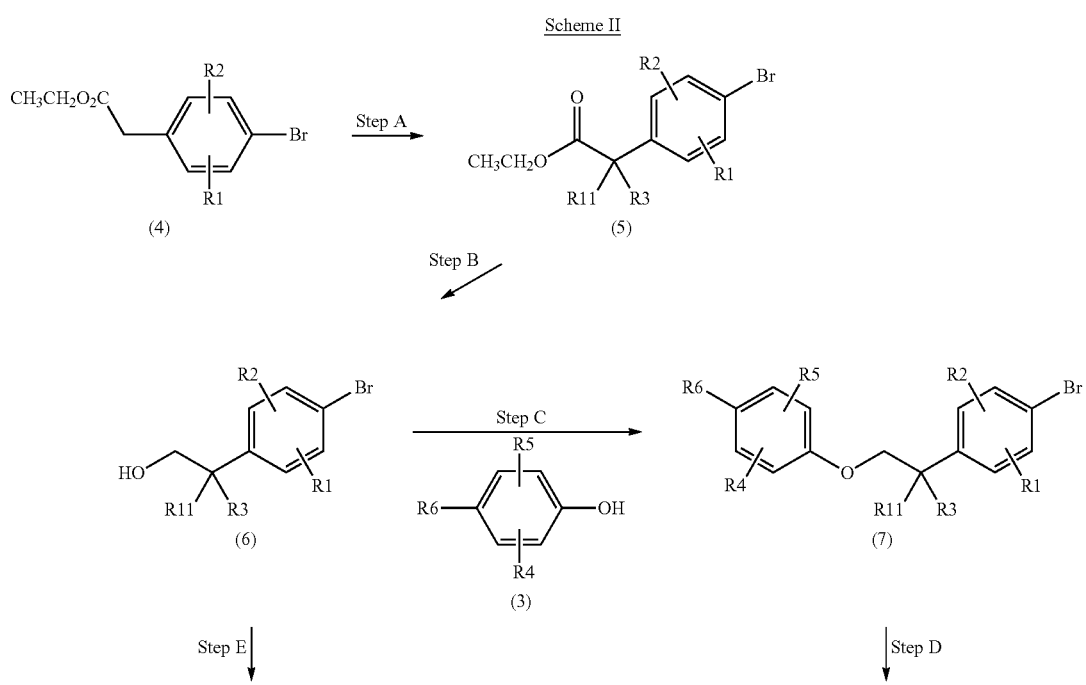

29

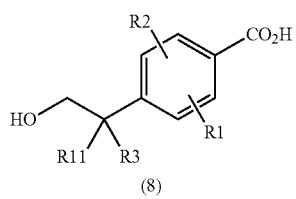
(8)

Step F ↓

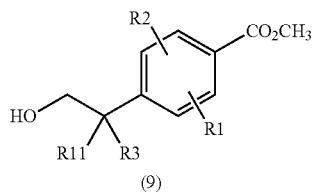
(9)

→ Step G

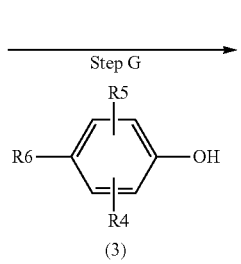
(3)

30

-continued

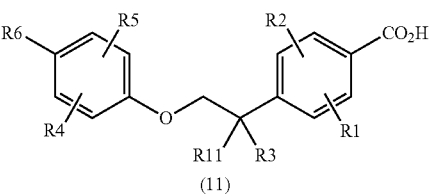

In Scheme II, Step A, a phenyl acetic acid ester of formula (4) is dialkylated to form a disubstituted phenyl acetic acid ester of formula (5), (wherein R11=R3). The unsubstituted ester is treated with two equivalents of a strong base such as sodium hydride, potassium hydride, lithium diisopropylamide or potassium tert-butoxide in the presence of a crown ether. Other potential bases include lithium, sodium, or potassium bis(trimethylsilyl)amide. The preferred conditions are sodium hydride in an inert solvent such as dimethylformamide or 1-methylpyrrolidinone and followed by alkylation with two equivalents of an alkyl halide (R3X) such as allyl bromide, iodomethane, iodoethane or the like. The reaction is performed at a temperature of 0° C. to room temperature for about 1 to 24 hours.

In Scheme II, Step B, the disubstituted ester of formula (5) is reduced to an alcohol of formula (6). Numerous methods for reducing carboxylic esters to alcohols are well known to those skilled in the art and can be found in the text of R. C. Larock in "Comprehensive Organic Transformations", VCH Publishers, 1989, p. 549-551. The preferred method is reduction with diisobutylaluminum hydride in an inert solvent such as dichloromethane. The reaction is performed at 0° C. to room temperature for 30 minutes to 24 hours. The reaction is worked up with tartaric acid solution and extracted using techniques known in the art, followed by purification using silica gel chromatography.

In Scheme II, Step C, an alcohol of formula (6) is coupled in a Mitsinobu reaction with a phenol of formula (3) (wherein R6=Ph(R7)(R8)(R9)), to give an ether of formula (7). Common redox systems, known to those skilled in the art, such as diethyl azodicarboxylate (DEAD)/triphenylphospine, N,N,N',N'-tetramethylazodicarboxamide (TMAD)/tributylphosphine or 1,1'-(azodicarbonyl)dipiperidine (ADDP)/tributylphosphine are used to effect the transformation. The preferred conditions use (ADDP)/triphenylphosphine, or alternatively (ADDP)/tributylphosphine, in an inert solvent at 0 to 100° C. for 2 to 24 hours. The product is isolated by techniques common to the skilled artisan such as silica gel chromatography.

In Scheme II, Step D, the phenyl bromide of formula (7) is carbonylated to form a benzoic acid of formula (11). The phenyl bromide is treated with two equivalents of tert-butyllithium at a temperature of −80 to −70° C. in an inert solvent such as tetrahydrofuran. The resulting phenyl lithiate is treated with carbon dioxide gas and allowed to warm to room temperature. The reaction is worked up using techniques common to one skilled in the art, such as quenching with acid and extracting with ethyl acetate, followed by silica gel chromatography.

In Scheme II, Step E, a hydroxyethyl phenyl bromide of formula (6) is carbonylated to a benzoic acid of formula (8). The hydroxylethyl phenyl bromide is treated sequentially, at −80 to −70° C., with one equivalent of n-butyllithium and two equivalents of tert-butyllithium. The dianion is treated with carbon dioxide gas and allowed to warm to room temperature. Isolation is effected by quenching with acid and extraction into an organic solvent, such as ethyl acetate. Purification is performed over a reverse phase C18 column.

In Scheme II, Step F, a benzoic acid of formula (8) is converted to a benzoic acid methyl ester of formula (9). The preferred conditions use an inorganic base, such as potassium carbonate or cesium carbonate in an inert solvent such as dimethylformamide with iodomethane. The reaction is performed at 0 to 50° C. for 2 to 24 hours. The product is isolated and purified by common extractive and chromatographic techniques.

In Scheme II, Step G, a hydroxy ethyl benzoic acid methyl ester of formula (9) is coupled in a Mitsinobu reaction to a phenol of formula (3), to give an ether of formula (10), using conditions similar to those as described for Scheme II, Step C, above.

In Scheme II, Step H, a benzoic acid methyl ester of formula (10) is hydrolyzed to form a benzoic acid of formula (11). The ester is hydrolyzed in an appropriate water soluble solvent such as ethanol, methanol, dioxane, or tetrahydrofuran, with tetrahydrofuran being preferred. The ester is treated with an inorganic base such as potassium, sodium or lithium hydroxide, with lithium hydroxide being preferred, at room temperature to the reflux temperature of the solvent for 2 to 48 hours. The benzoic acid of formula 11 is isolated by neutralization with hydrochloric acid followed by common extractive techniques.

Scheme III

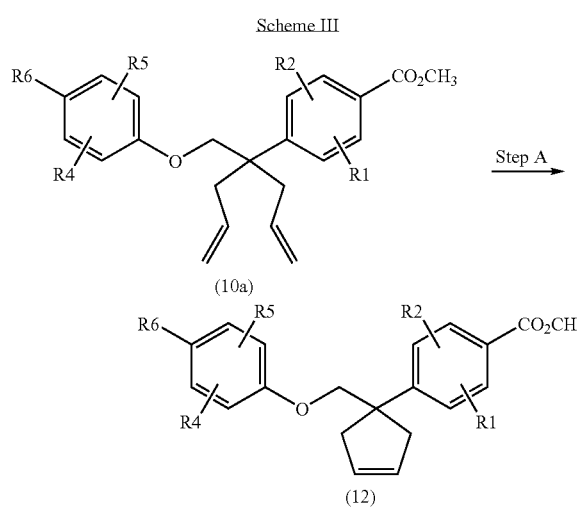

In Scheme III, Step A, a diallyl of formula (10a) (R11=R3=allyl) is cyclized in a ring-closing metathesis reaction to a cyclopentene of formula (12). The diallyl is treated with a Grubbs' catalyst such as 1,3-bis-(2,4,6-trimethylphenyl)-2-imidazolidinylidene) dichloro(phenylmethylene)-(tricyclohexylphosphine)ruthenium in an inert solvent such as dichloromethane at 0 to 50° C. for 30 min to 12 h. The ester of formula (12) is then hydrolyzed as described in Scheme II, Step H, for formula (10).

Scheme IV

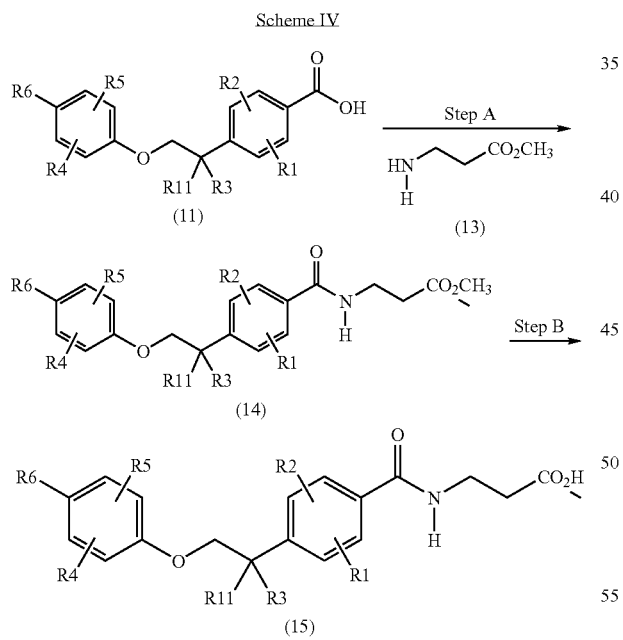

In Scheme IV, Step A, the benzoic acid of formula (11) is acylated to give the amide of formula (14). It will be recognized by one skilled in the art that there are numerous conditions for amide bond formation between a carboxylic acid and an amine. Such methods can be found in the text of R. C. Larock in "Comprehensive Organic Transformations", VCH Publishers, 1989, p. 972-976. The preferred conditions use 1-hydroxybenzotriazole hydrate (HOBt), 1, [3-(dimethylamino)propyl]-3-ethylcarbodiimide hydrochloride (EDCI) and an organic base such as diisopropylethylamine or triethylamine in an inert solvent such as dichloromethane, dimethylformamide, or tetrahydrofuran. The active ester is treated with an amine of formula (13) at 0 to 50° C., but preferably at room temperature, for about 4 to 48 hours.

Scheme V

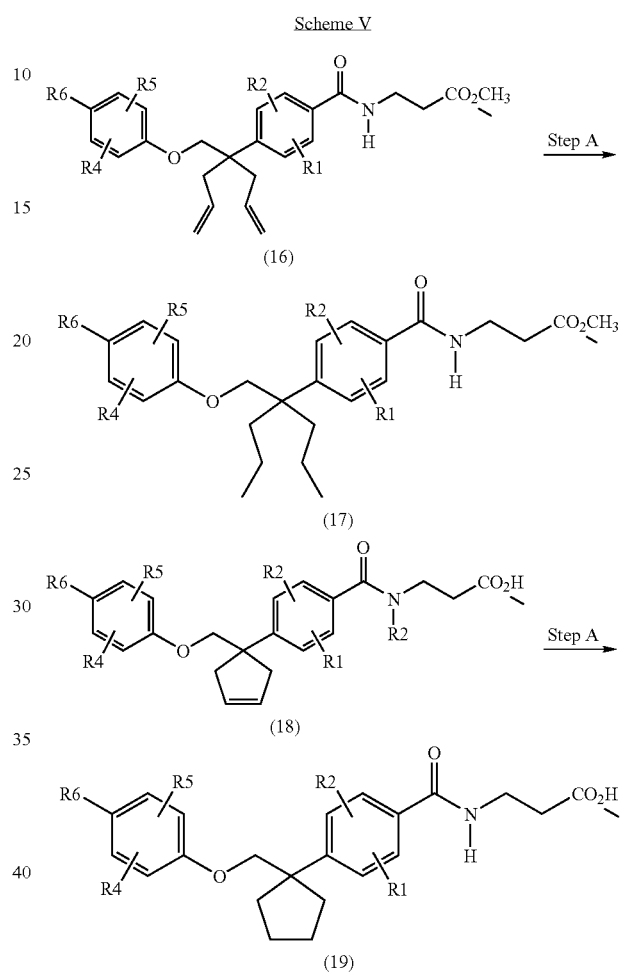

In Scheme V, Step A, a diallyl of formula (16) or cyclopentene of formula (18) is reduced to a dipropyl of formula (17) or a cyclopentane of formula (19). The olefinic bonds are reduced using 5 or 10% palladium on carbon in a solvent such as ethyl acetate, tetrahydrofuran, methanol or ethanol, with ethanol being preferred. The mixture is placed under hydrogen gas at 1 atm pressure for 4 to 24 hours. The crude reaction is filtered through Celite® to remove catalyst. The ester of formula (17) is then hydrolyzed to a carboxylic acid as described in Scheme IV, Step B for formula 14.

Scheme V

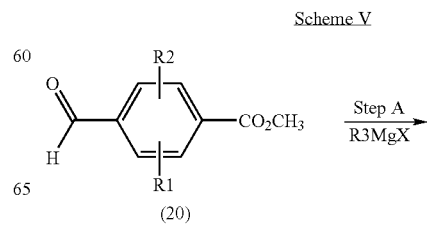

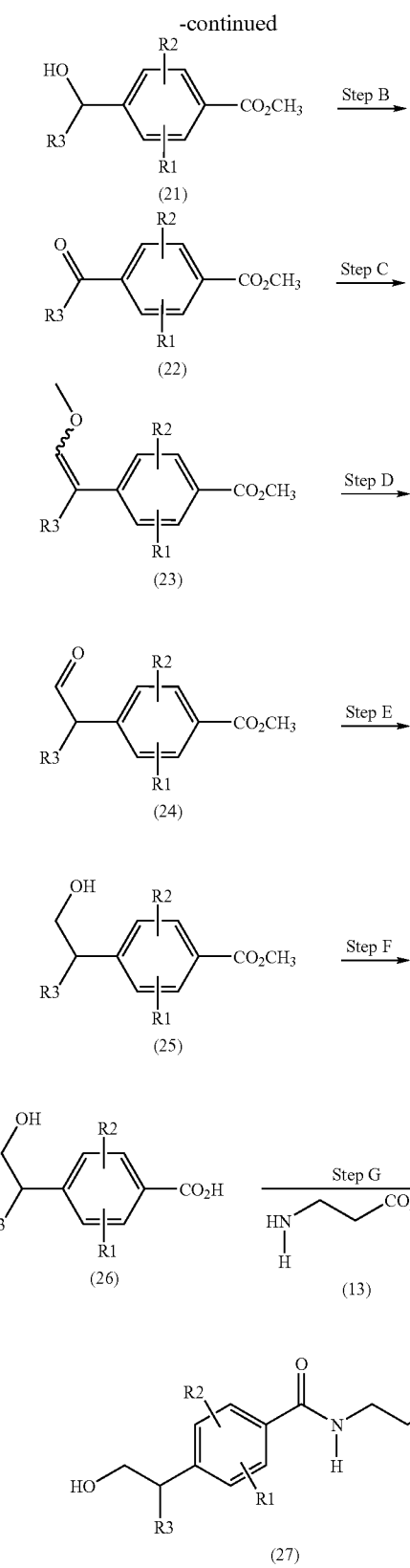

In Scheme V, Step B, a secondary alcohol of formula (21) is oxidized to a ketone of formula (22). There are numerous methods for oxidizing secondary alcohols which are recognized by one skilled in the art. Such methods include, but are not limited to, potassium permanganate, manganese (IV) oxide, ruthenium tetroxide, pyridium dichromate, Oxone®, o-iodobenzoic acid, Dess-Martin periodinane, tetrapropylammonium perruthenate (TPAP), and the like. The preferred conditions use pyridinium chlorochromate in an inert solvent such as dichloromethane at room temperature for about 2 to 48 hours.

In Scheme V, Step C a ketone of formula (22) is converted to a enol ether of formula (23) using (methoxymethyl)triphenylphosphonium chloride. The phosphorous ylide is generated with a strong base, such as potassium tert-butoxide in an inert solvent such as toluene or benzene followed by addition to the ketone of formula (22) at a temperature of 0° C. to the reflux temperature of the solvent, but preferably at room temperature. The product is isolated with common extractive techniques, such as quenching with a salt solution and extraction into an inert organic solvent.

In Scheme V, Step D, a enol ether of formula (23) is hydrolyzed to an aldehyde of formula (24). The skilled artisan will recognize that there are a variety of ways to effect this transformation with the use of formic, acetic, trifluoroacetic or p-toluenesulfonic acid. The preferred method uses concentrated hydrochloric acid in an inert solvent such as tetrahydrofuran. The product is isolated by neutralization with a concentrated inorganic base, such as potassium hydroxide, followed by extractive techniques to give the aldehyde of formula (24).

In Scheme V, Step E, an aldehyde of formula (24) is reduced to a primary alcohol of formula (25). A vast array of methods for reducing aldehydes are well known to those skilled in the art and can be found in the text of R. C. Larock in "Comprehensive Organic Transformations", VCH Publishers, 1989, p. 528-534. The preferred method is reduction with sodium borohydride in ethanol or methanol at room temperature to 60° C. for about 30 min to 24 hours.

In Scheme V, Step F, a benzoic acid methyl ester of formula (25) is hydrolyzed to a benzoic acid of formula (26). The ester is hydrolyzed in an appropriate water soluble solvent such as ethanol, methanol, dioxane, or tetrahydrofuran, with tetrahydrofuran being preferred. The ester is treated with an inorganic base such as potassium or sodium hydroxide, with sodium hydroxide being preferred, at room temperature to the reflux temperature of the solvent for 2 to 48 hours. The benzoic acid of formula (26) is isolated by neutralization with hydrochloric acid followed by common extractive techniques.

In Scheme V, Step 3, a benzoic acid of formula (26) is acylated to give the amide of formula (27). It will be recognized by one skilled in the art that there are numerous conditions for amide bond formation between a carboxylic acid and an amine. Such methods can be found in the text of R. C. Larock in "Comprehensive Organic Transformations", VCH Publishers, 1989, p. 972-976. The preferred conditions use 2-chloro-4,6-dimethoxy-1,3,5-triazine and an organic base such as 4-methylmorpholine in an inert solvent such as dichloromethane. After stirring for 2 to 24 hours, the active ester is treated with an amine of formula (13) at 0° C. to the reflux temperature of the solvent, but preferably at room temperature, for about 4 to 48 hours.

In Scheme V, Step A, a 4-formyl-benzoic acid methyl ester of formula (20) is reacted with a Grignard reagent (R3MgX where X=Cl or Br) to give a secondary alcohol of formula (21).

Scheme VI

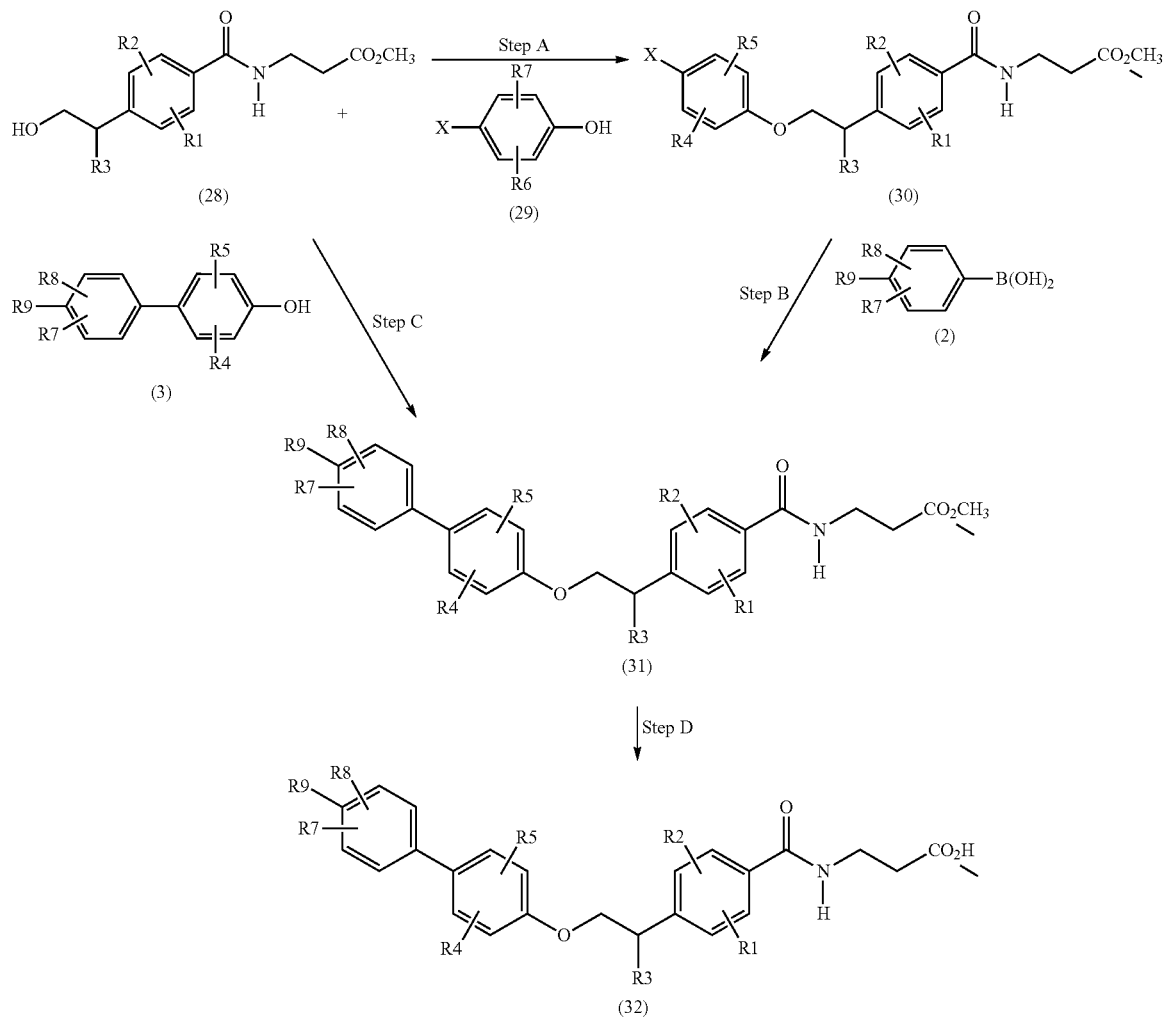

In Scheme VI, Step A, a secondary alcohol of formula (28) (wherein X=Br or I) is coupled in a Mitsinobu reaction with a phenol of formula (29), using conditions similar to those as described for Scheme III, Step C.

In Scheme VI, Step B, a 4-halophenylether of formula (30), is coupled with a phenyl boronic acid of formula (2), using a Suzuki reaction to provide a biphenyl ether of formula (31), using conditions similar to those as described for Scheme I, Step A.

Alternatively, in Scheme VI, Step C, a biphenyl hydroxy of formula (3), is coupled using Mitsinobu conditions described for Scheme VI, Step A to give a biphenyl ether of formula (31).

In Scheme VI, Step D, the ester of formula (31) is hydrolyzed to a the carboxylic acid of formula (32) using conditions as described in Scheme V, Step F.

PREPARATIONS AND EXAMPLES

The Examples provided herein are illustrative of the invention claimed herein and are not intended to limit the scope of the claimed invention in any way. Names of the preparations and examples are derived using ChemDraw.

$^1$H NMR spectra are recorded on a Varian 400 MHz spectrometer at ambient temperature. Data are reported as follows: chemical shift in ppm from internal standard tetramethylsilane on the (scale, multiplicity (b=broad, s=singlet, d=doublet, t=triplet, q=quartet, qn=quintet and m=multiplet), integration, coupling constant (Hz) and assignment. $^1$H-NMR indicates a satisfactory NMR spectrum was obtained for the compound described. Monoisotopic mass spectral data are obtained on an Agilent G1956B MSD single quadrapole instrument using electrospray ionization (ESI or ES). Analytical thin layer chromatography is performed on EM Reagent 0.25 mm silica gel 60-F plates. Visualization is accomplished with UV light. All examples are racemic unless indicated otherwise.

Preparation 1

4'-Trifluoromethyl-biphenyl-4-ol

Procedure A. A solution of 4-bromophenol (16.3 g, 94.3 mmol), 4-trifluoromethyl phenylboronic acid (19.7 g, 104 mmol), and potassium fluoride (11.0 g, 189 mmol) in 1:1 toluene:EtOH (378 mL) is treated with tetrakis(triphenylphosphine) palladium(0) (5.45 g, 4.71 mmol), warmed to reflux, and stirred overnight. The reaction mixture is cooled to room temperature, diluted with water, and extracted with EtOAc (3×). The combined organic extracts are dried over $Na_2SO_4$, filtered, and concentrated. The resulting solid is triturated with hexanes and filtered to provide 8.27 g (37%) of the title compound as a white solid. $^1H$ NMR ($CDCl_3$): δ 7.72-7.65 (m, 4H), 7.54-7.51 (m, 2H), 6.98-6.94 (m, 2H), 4.84 (s br, 1H).

Procedure B. 4-Bromophenol (5 g, 28.9 mmol), 4-trifluoromethyl phenyl boronic acid (6.59 g, 34.7 mmol), potassium carbonate (12 g, 86.7 mmol) and palladium (II) acetate (0.324 g, 1.445 mmol) are placed in water (50 mL), and the resulting mixture is stirred at room temperature overnight under open air. The mixture is filtered through Celite® and extracted with ethyl acetate (3×200 ml). The combined organic layers are washed with water, 1N HCl, water, brine, dried ($MgSO_4$), and concentrated. The resulting material is purified by silica gel chromatography to yield the title compound as a white solid (6.0 g, 87%).

Preparation 2

2,6-Dimethyl-4'-trifluoromethyl-biphenyl-4-ol

To a solution of 4-iodo-3,5-dimethyl-phenol (3.35 g, 13.5 mmol) in THF (81 ml) is added (4-trifluoromethyl)phenylboronic acid (3.35 g, 16.2 mmol), potassium fluoride (1.94 mg, 40.6 mmol), palladium(II) acetate (152 mg, 0.67 mmol), and (oxydi-2,1-phenylene)bis-(diphenylphosphine) (730 mg, 1.35 mmol). The reaction mixture is heated to reflux overnight. After cooling to room temperature, the reaction mixture is partitioned between ethyl acetate and water. The aqueous layer is back-extracted with ethyl acetate, the combined organic layers are dried and concentrated. The resulting residue is applied to silica gel and eluted using hexanes with an ethyl acetate gradient from 0% to 70% to give the title compound (3.3 g).

Preparation 3

4-[1-Allyl-1-(2,6-dimethyl-4'-trifluoromethyl-biphenyl-4-yloxymethyl)-but-3-enyl]-benzoic acid methyl ester Step A. 2-Allyl-2-(4-bromo-phenyl)-pent-4-enoic acid ethyl ester A solution of (4-bromo-phenyl)-acetic acid ethyl ester (2.014 g, 8.26 mmol) in DMF (40 mL) at 0° C. is treated with NaH (60% dispersion in mineral oil, 0.739 g, 18.5 mmol), allylbromide (1.70 mL, 19.6 mmol), and warmed to room temperature for 1 h. The reaction mixture is placed in a cold water bath, diluted with water (100 mL), and extracted with EtOAc (3×75 mL). The combined organic extracts are washed with water, brine, dried over $MgSO_4$, filtered, and concentrated to provide 2.64 g of the title compound as a clear oil. The crude material is taken onto the next step without further purification.

Step B. 2-Allyl-2-(4-bromo-phenyl)-pent-4-en-1-ol

A solution of crude 2-allyl-2-(4-bromo-phenyl)-pent-4-enoic acid ethyl ester (2.64 g) in $CH_2Cl_2$ (40 mL) at 0° C. is treated with diisobutylaluminum hydride (1.0 M toluene, 17.5 mL) dropwise for 8 min, warmed to room temperature, and stirred for 45 min. The reaction mixture is cooled to 0° C., quenched with 1M tartaric acid (25 mL), and stirred overnight. The organic layer is separated and the aqueous layer is extracted with $CH_2Cl_2$ (3×25 mL). The combined organic extracts are dried over $MgSO_4$, filtered, and concentrated. The residue is loaded onto silica gel and eluted with hexanes using a gradient of 0% EtOAc to 50% EtOAc to provide 1.319 g (56%-2 steps) of the title compound as a light yellow oil. $^1H$ NMR ($CDCl_3$): δ 7.47-7.43 (m, 2H), 7.23-7.19 (m, 2H), 5.59 (ddt, J=17.1, 10.2, 6.7 Hz, 2H), 5.09-5.01 (m, 4H), 3.76 (d, J=6.8 Hz, 2H), 2.48 (dd, J=14.1, 6.8 Hz), 2.42 (dd, J=13.6, 7.2 Hz, 2H), 1.29 (t, J=6.1 Hz).

Step C.
4-(1-Allyl-1-hydroxymethyl-but-3-enyl)-benzoic acid

A solution of 2-allyl-2-(4-bromo-phenyl)-pent-4-en-1-ol (1.30 g, 4.64 mmol) in THF (46 mL) at −78° C. is treated with n-butyllithium (2.0 mL, 2.5 M in hexanes, 5.0 mmol) and stirred for 30 min. The reaction mixture is then treated with tert-butyllithium (1.7 M pentane, 6.0 mL, 10.2 mmol) dropwise over 12 min. After 14 min, $CO_2$ (g) is bubbled through the solution and the reaction is warmed to room temperature. The reaction mixture is poured into 1N HCl (25 mL) and extracted with EtOAc (3×50 mL). The combined extracts are dried over $MgSO_4$, filtered, and concentrated. The residue is loaded onto C18 and eluted with water using a gradient of 15% acetonitrile to 100% acetonitrile to provide 0.793 g (69%) of the title compound as a white solid. MS (ES): 245.1 $[M-H]^-$.

Step D.
4-(1-Allyl-1-hydroxymethyl-but-3-enyl)-benzoic acid methyl ester

A solution of 4-(1-allyl-1-hydroxymethyl-but-3-enyl)-benzoic acid (0.793 g, 3.22 mmol) in DMF (11.0 mL) is treated with $K_2CO_3$ (0.685 g, 4.96 mmol), and iodomethane (0.25 mL, 4.02 mmol), and stirred at room temperature overnight. The mixture is poured into water (25 mL) and extracted with EtOAc (3×25 mL). The combined extracts are washed with water, brine, dried over $MgSO_4$, filtered, and concentrated. The residue is loaded onto silica gel and eluted with hexanes using a gradient of 0% to 75% EtOAc to give 0.774 g, (92%) of the title compound as a clear syrup. $^1H$ NMR ($CDCl_3$): δ 8.03-8.00 (m, 2H), 7.44-7.41 (m, 2H), 5.65-5.54 (m, 2H), 5.11-5.06 (m, 4H), 5.05-5.02 (m, 4H), 3.91 (s, 3H), 3.84 (d, 2H, J=6.2 Hz), 2.59-2.46 (m, 4H), 1.33 (t, 1H, J=6.2 Hz).

Step E. 4-[1-Allyl-1-(2,6-dimethyl-4'-trifluoromethyl-biphenyl-4-yloxymethyl)-but-3-enyl]-benzoic acid methyl ester A solution of 4-(1-allyl-1-hydroxymethyl-but-3-enyl)-benzoic acid methyl ester (0.768 g, 2.95 mmol), 2,6-dimethyl-4'-trifluoromethyl-biphenyl-4-ol (0.861 g, 3.23 mmol), and triphenylphosphine (1.180 g, 4.50 mmol) in toluene (30 mL) is treated with 1,1'-(azodicarbonyl)-dipiperidine (1.182 g, 4.68 mmol) and stirred overnight at 80° C. The reaction mixture is then cooled to room temperature, diluted with MeOH, and concentrated. The residue is loaded onto silica gel and eluted with hexanes using a gradient of 0% EtOAc to 40% EtOAc to provide 0.964 g (64%) of the title compound as a clear syrup. $^1H$ NMR ($CDCl_3$): δ 8.02-8.00 (m, 2H), 7.67 (d, J=8.0 Hz, 2H), 7.46-7.44 (m, 2H), 7.26 (d, J=7.8 Hz, 2H), 6.68 (s, 2H), 5.60-5.54 (m, 2H), 5.08-5.00 (m, 4H), 4.15 (s, 2H), 3.91 (s, 3H), 2.66 (d, J=7.6 Hz, 4H), 1.99 (s, 6H).

Preparation 4

4-[2-(2,6-Dimethyl-4'-trifluoromethyl-biphenyl-4-yloxy)-1,1-dimethyl-ethyl]-benzoic acid methyl ester The title compound is prepared by essentially following the procedures as described in Preparation 3, by substituting allyl bromide with iodomethane in Preparation 3, Step A.
$^1$H NMR (CDCl$_3$): δ 8.02-7.99 (m, 2H), 7.66 (d, J=8.1 Hz, 2H), 7.53-7.49 (m, 2H), 7.24 (d, J=8.0 Hz, 2H), 6.64 (s, 2H), 3.98 (s, 2H), 3.91 (s, 3H), 1.96 (s, 6H), 1.49 (s, 6H).

Preparation 5

4-[2-(2,6-Dimethyl-4'-trifluoromethyl-biphenyl-4-yloxymethyl)-1-ethyl-propyl]-benzoic acid methyl ester The title compound is prepared by essentially following the procedures as described in Preparation 3, by substituting allyl bromide with iodoethane in Preparation 3, Step A. $^1$H NMR (CDCl$_3$): δ 8.02-7.98 (m, 2H), 7.66 (d, J=8.1 Hz, 2H), 7.44-7.41 (m, 2H), 7.25 (d, J=7.8 Hz, 2H), 6.70 (s, 2H), 4.16 (s, 2H), 3.91 (s, 3H), 1.99 (s, 6H), 1.95-1.89 (m, 4H), 0.74 (t, J=6.9 Hz, 6H).

Preparation 6

4-[1-(2,6-Dimethyl-4'-trifluoromethyl-biphenyl-4-yloxymethyl)-cyclopent-3-enyl]-benzoic acid methyl ester A solution of 4-[1-allyl-1-(2,6-dimethyl-4'-trifluoromethyl-biphenyl-4-yloxymethyl)-but-3-enyl]-benzoic acid methyl ester (6.0 mL of 0.11M stock solution in CH$_2$Cl$_2$, 0.578 g, 1.14 mmol) in CH$_2$Cl$_2$ (570 mL) is treated with [1,3-bis-(2,4,6-trimethylphenyl)-2-imidazolidinylidene]dichloro(phenylmethylene)-(tricyclohexylphosphine)ruthenium] (0.101 g, 0.1192 mmol) at 35° C. for 1 h, cooled to room temperature, and concentrated. The residue is loaded onto silica gel and eluted using hexanes with an ethyl acetate gradient from 0% to 40% to afford the title compound (0.458 g, 84%) as a colorless syrup. $^1$H NMR (CDCl$_3$): δ 7.98-7.96 (m, 2H), 7.63 (d, J=8.3 Hz, 2H), 7.44-7.41 (m, 2H), 7.20 (d, J=8.1 Hz, 2H), 6.58 (s, 2H), 5.77 (s, 2H), 3.99 (s, 2H), 3.89 (s, 3H), 2.87 (d, J=14.3 Hz, 2H), 2.77 (d, J=14.9 Hz, 2H), 1.92 (s, 6H).

Example 1

3-{4-[1-Allyl-1-(4'-trifluoromethyl-biphenyl-4-yloxymethyl)-but-3-enyl]-benzoylamino}-propionic acid

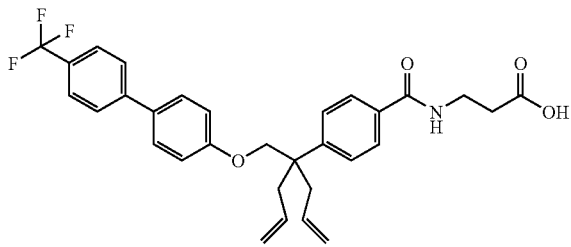

Step C. 4-[2-Allyl-2-(4-bromo-phenyl)-pent-4-enyloxy]-4'-trifluoromethyl-biphenyl A solution of 2-allyl-2-(4-bromo-phenyl)-pent-4-en-1-ol (from Preparation 3, Step B)(0.206 g, 0.734 mmol), 4'-trifluoromethyl-biphenyl-4-ol (0.184 g, 0.772 mmol), and triphenylphosphine (0.286 g, 1.09 mmol) in toluene (7.0 mL) is treated with 1,1'-(azodicarbonyl)-dipiperidine (0.272 g, 1.08 mmol) and stirred overnight at room temperature. The reaction is then warmed to 80° C. for 6 h, cooled to room temperature, diluted with MeOH, and concentrated. The residue is loaded onto silica gel and eluted with hexanes using a gradient of 0% EtOAc to 50% EtOAc to provide 0.226 g, (61%) of the title compound as a yellow syrup. $^1$H NMR (CDCl$_3$): δ 7.66-7.61 (m, 4H), 7.52-7.50 (m, 2H), 7.46-7.44 (m, 2H), 7.24-7.22 (m, 2H), 7.00-6.98 (m, 2H), 5.56 (ddt, J=17.1, 10.3, 7.2 Hz, 2H), 5.05-4.99 (m, 4H), 4.12 (s, 2H), 2.61 (d, J=7.4 Hz, 4H).

Step D. 4-[1-Allyl-1-(4'-trifluoromethyl-biphenyl-4-yloxymethyl)-but-3-enyl]-benzoic acid A solution of 4-[2-allyl-2-(4-bromo-phenyl)-pent-4-enyloxy]-4'-trifluoromethyl-biphenyl (0.218 g, 0.434 mmol) in THF (4.0 mL) at −78° C. is treated with tert-butyl lithium (1.7 M pentane, 0.55 mL, 0.935 mmol) dropwise. After 10 min, carbon dioxide gas is bubbled through the solution and the reaction is warmed to room temperature. The reaction mixture is diluted with water (10 mL), acidified with 1N HCl (1.0 mL), and extracted with EtOAc (3×20 mL). The combined extracts are dried over MgSO$_4$, filtered, and concentrated. The residue is loaded onto silica gel and eluted with hexanes using a gradient of 0% EtOAc to 100% EtOAc to provide 0.044 g (22%) of the title compound as a white foam. MS (ES): 465.2 [M−H]$^−$.

Step E. 3-{4-[1-Allyl-1-(4'-trifluoromethyl-biphenyl-4-yloxymethyl)-but-3-enyl]-benzoylamino}-propionic acid methyl ester A solution of 4-[1-allyl-1-(4'-trifluoromethyl-biphenyl-4-yloxymethyl)-but-3-enyl]-benzoic acid (0.044 g, 0.094 mmol), beta-alanine, hydrochloride salt (0.0189 g, 0.135 mmol), and 1-hydroxybenzotriazole hydrate (0.0193 g, 0.143 mmol) in DMF (2.0 mL) is treated with N,N-diisopropylethylamine (0.0480 mL, 0.275 mmol), then 1-(3-dimethylaminopropyl)-3-ethylcarbodiimide hydrochloride (0.0278 g, 0.145 mmol) and stirred overnight. The reaction mixture is diluted with water (5 mL) and extracted with EtOAc (3×10 mL). The combined organic extracts are washed with water, brine, dried over MgSO$_4$, filtered, and concentrated. The residue is loaded onto silica gel and eluted with hexanes using a gradient of 10% EtOAc to 75% EtOAc to provide 0.0298 g (58%) of the title compound as a clear film. MS (ES): 552.2 [M+H]$^−$.

Step F. 3-{4-[1-Allyl-1-(4'-trifluoromethyl-biphenyl-4-yloxymethyl)-but-3-enyl]-benzoylamino}-propionic acid A solution of 3-{4-[1-allyl-1-(4'-trifluoromethyl-biphenyl-4-yloxymethyl)-but-3-enyl]-benzoylamino}-propionic acid methyl ester (0.0279 g, 0.0506 mmol) in THF (1.0 mL) is treated with 1N LiOH (1.0 mL) and stirred overnight at room temperature. The reaction mixture is acidified with 1N HCl (2.2 mL) and extracted with EtOAc (3×10 mL). Combined extracts are dried over MgSO$_4$, filtered, and concentrated to provide 3-{4-[1-allyl-1-(4'-trifluoromethyl-biphenyl-4-yloxymethyl)-but-3-enyl]-benzoylamino}-propionic acid (0.0189 g, 69%) as a white solid. MS (ES): 538.3 [M+H]$^+$.

Example 2

3-{4-[1-Allyl-1-(2,6-dimethyl-4'-trifluoromethyl-biphenyl-4-yloxymethyl)-but-3-enyl]-benzoylamino}-propionic acid

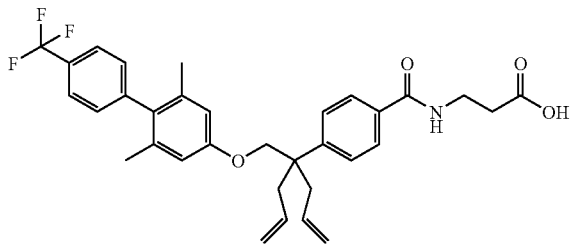

Step A. 4-[1-Allyl-1-(2,6-dimethyl-4'-trifluoromethyl-biphenyl-4-yloxymethyl)-but-3-enyl]-benzoic acid A solution of 4-[1-allyl-1-(2,6-dimethyl-4'-trifluoromethyl-biphenyl-4-yloxymethyl)-but-3-enyl]-benzoic acid methyl ester (0.386 g, 0.758 mmol) in THF (8.0 mL) is treated with 1N LiOH (8.0 mL, 8.0 mmol), warmed to 70° C., and stirred overnight. The reaction mixture is cooled to room temperature, acidified with 1N HCl (9.0 mL), and extracted with EtOAc (3×20 mL). The combined extracts are dried over MgSO$_4$, filtered, and concentrated to provide 0.356 g (95%) of the title compound as a white foam. MS (ES): 493.3 [M−H]$^-$.

Step B. 3-{4-[1-Allyl-1-(2,6-dimethyl-4'-trifluoromethyl-biphenyl-4-yloxymethyl)-but-3-enyl]-benzoylamino}-propionic acid methyl ester To a mixture of 4-[1-allyl-1-(2,6-dimethyl-4'-trifluoromethyl-biphenyl-4-yloxymethyl)-but-3-enyl]-benzoic acid (0.349 g, 0.705 mmol), 3-amino-propionic acid methyl ester hydrochloride (0.112 g, 0.804 mmol), and 1-hydroxybenzotriazole hydrate (HOBt, 0.121 g, 0.898 mmol) in DMF (7.0 mL) is added N,N-diisopropylethylamine (0.38 mL, 2.2 mmol), then N-(3-dimethylaminopropyl)-N'-ethylcarbodiimide hydrochloride (EDCI, 0.180 g, 0.938 mmol) and stirred overnight. The reaction mixture is poured into water (25 mL) and extracted with EtOAc (3×25 mL). The combined organic extracts are washed with water, brine, dried over MgSO$_4$, filtered, and concentrated. The residue is loaded onto silica gel and eluted using hexanes with an ethyl acetate gradient from 0% to 75% to provide 0.296 g (72%) of the title compound as a white foam. MS (ES): 580.4 [M+H]$^+$.

Step C. 3-{4-[1-Allyl-1-(2,6-dimethyl-4'-trifluoromethyl-biphenyl-4-yloxymethyl)-but-3-enyl]-benzoylamino}-propionic acid A solution of 3-{4-[1-allyl-1-(2,6-dimethyl-4'-trifluoromethyl-biphenyl-4-yloxymethyl)-but-3-enyl]-benzoylamino}-propionic acid methyl ester (0.0438 g, 0.0756 mmol) in THF (1.0 mL) is treated with 1N LiOH (1.0 mL) and stirred overnight at room temperature. The reaction mixture is acidified with 1N HCl (1.1 mL), diluted with water (5 mL), and extracted with EtOAc (3×10 mL). The combined extracts are dried over MgSO$_4$, filtered, and concentrated to provide 0.0105 g (24%) of the title compound as a white solid. MS (ES): 566.4 [M+H]$^+$.

Example 3

3-{4-[2-(2,6-Dimethyl-4'-trifluoromethyl-biphenyl-4-yloxy)-1,1-dimethyl-ethyl]-benzoylamino}-propionic acid

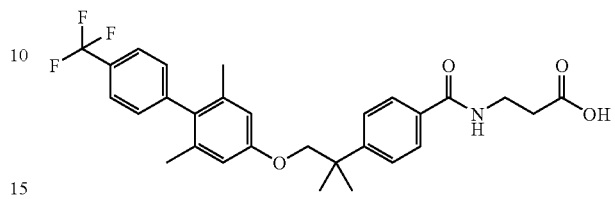

The title compound is prepared by essentially following the procedures as described in Example 2, using 4-[2-(2,6-dimethyl-4'-trifluoromethyl-biphenyl-4-yloxy)-1,1-dimethyl-ethyl]-benzoic acid methyl ester as the starting material. MS (ES): δ 14.3 [M+H]$^+$.

Example 4

3-{4-[1-(2,6-Dimethyl-4'-trifluoromethyl-biphenyl-4-yloxymethyl)-1-ethyl-propyl]-benzoylamino}-propionic acid

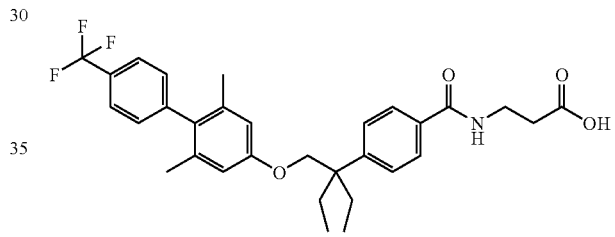

The title compound is prepared by essentially following the procedures as described in Example 2 using 4-[1-(2,6-dimethyl-4'-trifluoromethyl-biphenyl-4-yloxymethyl)-1-ethyl-propyl]-benzoic acid methyl ester as the starting material. MS (ES): 542.4[M+H]$^+$.

Example 5

3-{4-[1-(2,6-dimethyl-4'-trifluoromethyl-biphenyl-4-yloxymethyl)-cyclopent-3-enyl]-benzoylamino}-propionic acid

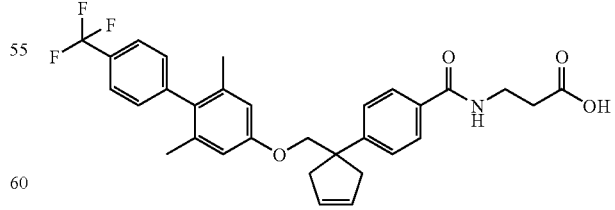

The title compound is prepared by essentially following the procedures as described in Example 2 using 4-[1-(2,6-dimethyl-4'-trifluoromethyl-biphenyl-4-yloxymethyl)-cyclopent-3-enyl]-benzoic acid methyl ester as the starting material. MS (ES): 538.3 [M+H]$^+$.

Example 6

3-{4-[1-(2,6-Dimethyl-4'-trifluoromethyl-biphenyl-4-yloxymethyl)-cyclopentyl]-benzoylamino}-propionic acid

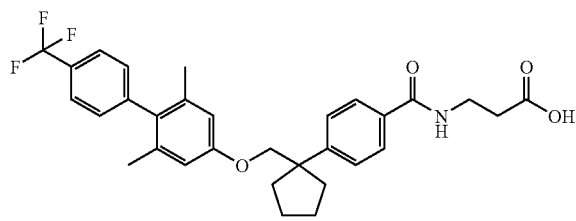

A solution of 3-{4-[1-(2,6-dimethyl-4'-trifluoromethyl-biphenyl-4-yloxymethyl)-cyclopent-3-enyl]-benzoylamino}-propionic acid (0.134 g, 0.250 mmol) in EtOH (3.0 mL) is treated with 10% palladium on carbon (26.7 mg), flushed with hydrogen, and stirred under 1 atm pressure overnight. The mixture is then filtered through Celite® and concentrated to provide 0.0350 g (26%) of the title compound as a clear syrup. MS (ES): 540.4 [M+H]$^+$.

Example 7

3-{4-[1-Propyl-1-(4'-trifluoromethyl-biphenyl-4-yloxymethyl)-butyl]-benzoylamino}-propionic acid

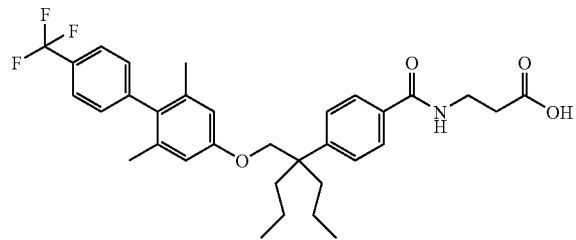

Step A. 3-{4-[1-Propyl-1-(4'-trifluoromethyl-biphenyl-4-yloxymethyl)-butyl]-benzoylamino}-propionic acid methyl ester A solution of 3-{4-[1-allyl-1-(4'-trifluoromethyl-biphenyl-4-yloxymethyl)-but-3-enyl]-benzoylamino}-propionic acid methyl ester (0.0731 g, 0.126 mmol) in EtOH (4.0 mL) is treated with 10% palladium on carbon (16 mg), flushed with hydrogen, and stirred under 1 atm pressure overnight. The mixture is then filtered through Celite® and concentrated to provide 0.0703 g (96%) of the title compound as a clear syrup. MS (ES): 84.4 [M+H]$^+$.

Step B. 3-{4-[1-Propyl-1-(4'-trifluoromethyl-biphenyl-4-yloxymethyl)-butyl]-benzoylamino}-propionic acid A solution of 3-{4-[1-allyl-1-(4'-trifluoromethyl-biphenyl-4-yloxymethyl)-but-3-enyl]-benzoylamino}-propionic acid methyl ester (0.0703 g, 0.120 mmol) in THF (2.0 mL) is treated with 1N LiOH (2.0 mL) and stirred overnight at room temperature. The reaction mixture is acidified with 1N HCl (2.2 mL) and extracted with EtOAc (3×10 mL). The combined extracts are dried over MgSO$_4$, filtered, and concentrated to provide 0.0401 g, (58%) of the title compound as a white solid. MS (ES): 570.4 [M+H]$^+$.

Preparation 7

4-(3-Methyl-butyryl)-benzoic acid methyl ester

Step A. Racemic 4-(1-Hydroxy-3-methyl-butyl)-benzoic acid methyl ester

A solution of 4-formyl-benzoic acid methyl ester (32.4 g, 147 mmol) in anhydrous THF (800 mL) is cooled to 0° C. while stirring under nitrogen. Isobutyl magnesium bromide (2.0M in diethyl ether, 110 mL, 221 mmol) is added slowly over 10 min. The reaction is allowed to stir at 0° C. for 1 h, and then allowed to warm to room temperature. The reaction is monitored by HPLC, and upon complete consumption of the aldehyde, the reaction is quenched carefully with 1N HCl. The reaction is diluted with diethyl ether and water, followed by extraction. The organic layer is washed with water and brine, followed by drying over anhydrous sodium sulfate. The solution is filtered and concentrated, then further purified using flash column chromatography using ethyl acetate/hexanes to provide 12 g (37%) of product.

Step B. 4-(3-Methyl-butyryl)-benzoic acid methyl ester

To a solution of 4-(1-hydroxy-3-methyl-butyl)-benzoic acid methyl ester (19.72 g, 88.78 mmol) in dichloromethane (300 mL) is added pyridinium chlorochromate (22.03 g, 97.65 mmol). The mixture is allowed to stir at room temperature, and the solution turns black over time. The reaction is monitored by HPLC. Upon complete conversion, the reaction is diluted with dichloromethane and silica gel (2% by weight) is added to the mixture. The mixture is purified by flash column chromatography using dichloromethane as mobile phase, producing 15.79 g (72%) of product. MS (ES): 221.3 (M+1)$^+$.

The ketones in the table below are prepared by essentially following the procedures as described in Preparation 7, Steps A and B, using either the commercially available Grignard reagent, or generating it from the corresponding halide, in Preparation 7, Step A.

| Prep | Starting Grignard | Product name | Structure |
| --- | --- | --- | --- |
| 8 | n-Hexylmagnesium bromide | 4-Heptanoyl-benzoic acid methyl ester | 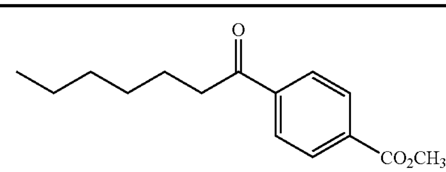 |

| Prep | Starting Grignard | Product name | Structure |
|---|---|---|---|
| 9 | Isobutylmagnesium chloride | 4-(3-Methyl-butyryl)-benzoic acid methyl ester | 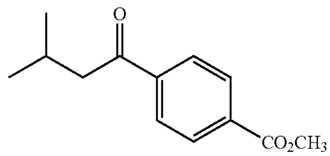 |
| 10 | n-Butylmagnesium chloride | 4-Butyryl-benzoic acid methyl ester | 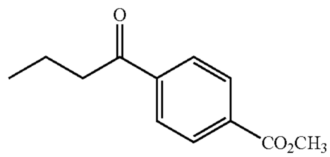 |
| 11 | 1,1,1-Trifluoro-butane-4-magnesium bromide | 4-(5,5,5-Trifluoro-pentanoyl)-benzoic acid methyl ester | 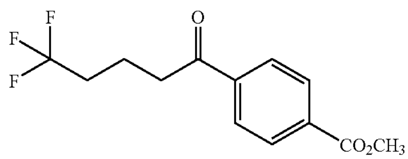 |
| 12 | 3,3,3-trifluoropropyl magnesium bromide | 4-(4,4,4-Trifluoro-butyryl)-benzoic acid methyl ester | 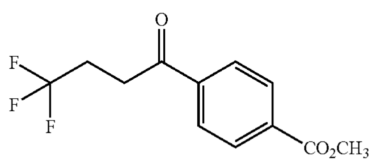 |
| 13 | Isopropylmagnesium chloride | 4-Isobutyryl-benzoic acid methyl ester | 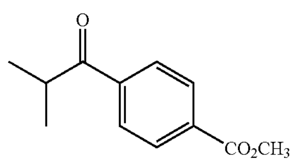 |

Preparation 14

3-[4-(1-Hydroxymethyl-heptyl)-benzoylamino]-propionic acid methyl ester

Step A. 4-(1-Methoxymethylene-heptyl)-benzoic acid methyl ester (Methoxymethyl)triphenylphosphonium chloride (10.34 g, 30.24 mmol) is suspended in anhydrous toluene (75 mL) and potassium tert-butoxide (3.39 g, 30.24 mmol) is carefully added. The solution is allowed to stir at room temperature for 4 h. 4-Heptanoyl-benzoic acid methyl ester (5.0 g, 20.16 mmol) is then dissolved in anhydrous toluene (25 mL) and added to the reaction mixture by cannula. The reaction is allowed to stir at room temperature overnight and is monitored by TLC. Upon complete consumption of starting material, the reaction is carefully quenched with saturated ammonium chloride solution, extracted with diethyl ether, washed, dried, and concentrated. The title compound is purified by column chromatography using hexanes/ethyl acetate and used directly in the next step.

Step B. 4-(1-Formyl-heptyl)-benzoic acid methyl ester 4-(1-Methoxymethylene-heptyl)-benzoic acid methyl ester (3.5 g, 12.68 mmol) is dissolved in tetrahydrofuran (50 mL) and concentrated hydrochloric acid (5 mL) is added. The system is purged of air with nitrogen and heated to reflux for 6 h. The reaction is monitored by HPLC. The reaction is allowed to cool to room temperature and then neutralized with 30% potassium hydroxide solution and bicarbonate. The two phases are separated and the aqueous extracted a second time with diethyl ether. The combined organic extracts are washed with brine, dried over sodium sulfate, and concentrated. The crude material is loaded onto a silica gel column and purified using hexanes/ethyl acetate. MS (ES): 261.2 [M+H]−.

Step C. 4-(1-Hydroxymethyl-heptyl)-benzoic acid methyl ester 4-(1-Formyl-heptyl)-benzoic acid methyl ester (3.17 g, 12.1 mmol) is dissolved in ethanol (50 mL) and allowed to stir under nitrogen in an ice bath at 0° C. Sodium borohydride (0.457 g, 12.1 mmol) is added to the mixture in one portion. The reaction is allowed to stir at 0° C. for one hour, then warmed slowly to room temperature for several hours and is monitored by TLC. Upon complete consumption of starting material, the reaction is carefully quenched with water and the ethanol is removed in vacuo. The remaining mixture is diluted with ethyl acetate. The two phases are separated, and the organic layer washed, dried, and concentrated. The title compound is used in the next step without further purification. MS (ES): 265.2 [M+H]+.

Step D. 4-(1-Hydroxymethyl-heptyl)-benzoic acid 4-(1-Hydroxymethyl-heptyl)-benzoic acid methyl ester (3.46 g, 12.1 mmol) is dissolved in tetrahydrofuran (40 mL) and 5N sodium hydroxide (10 mL) is added. The reaction may be monitored by HPLC and is complete within 8 h. The reaction is neutralized with 5N HCl (10 mL), and diluted with diethyl ether and water. The two phases are separated, and the organic layer is washed, dried, and concentrated to provide the title compound which is used without further purification. MS (ES): 249.3 [M+H]−.

Step E. 3-[4-(1-Hydroxymethyl-heptyl)-benzoylamino]-propionic acid methyl ester 4-(1-Hydroxymethyl-heptyl)-benzoic acid (500 mg, 2.00 mmol), 2-chloro-4,6-dimethoxy-1,3,5-triazine (362 mg, 2.06 mmol), and 4-methylmorpholine (230 µL, 2.10 mmol) are combined in anhydrous dichloromethane (10 mL) under nitrogen. The reaction is allowed to stir under nitrogen at room temperature overnight. Beta-alanine methyl ester hydrochloride (306 mg, 2.20 mmol) is added to the reaction mixture, followed by more 4-methyl morpholine (460 µL, 4.2 mmol), and allowed to stir at room temperature. Some water (<10% volume) is added to help solubility. The reaction is monitored by HPLC, and after 4 h, the reaction is diluted with more dichloromethane. The reaction is diluted with water and rinsed with 1N HCl. Upon acidification, the two layers are separated. The organic layer is washed with brine, dried over anhydrous sodium sulfate, and concentrated. The resulting residue is purified by flash column chromatography with hexanes/ethyl acetate to provide the title compound. MS (ES): 334.2 [M+H]−.

Preparation 15

3-[4-(1-Hydroxymethyl-3-methyl-butyl)-benzoylamino]-propionic acid methyl ester The title compound is prepared by essentially following the procedures as described in Preparation 14, using 4-(3-methyl-butyryl)-benzoic acid methyl ester as the starting material. MS (ES): 306.2 [M+H]−.

Preparation 16

3-[4-(1-Hydroxymethyl-butyl)-benzoylamino]-propionic acid methyl ester

The title compound is prepared by essentially following the procedures as described in Preparation 14, using 4-butyryl-benzoic acid methyl ester as the starting material. MS (ES): 292.2 [M+H]−.

Preparation 17

3-[4-(5,5,5-Trifluoro-1-hydroxymethyl-pentyl)-benzoylamino]-propionic acid methyl ester The title compound is prepared by essentially following the procedures as described in Preparation 14, using 4-(5,5,5-trifluoro-pentanoyl)-benzoic acid methyl ester as the starting material. MS (ES): 360.3 [M+H]−.

Preparation 18

3-[4-(4,4,4-Trifluoro-1-hydroxymethyl-butyl)-benzoylamino]-propionic acid methyl ester The title compound is prepared by essentially following the procedures as described in Preparation 14, using 4-(4,4,4-trifluoro-butyryl)-benzoic acid methyl ester as the starting material. MS (ES): 346.3 [M+H]−.

Preparation 19

3-[4-(1-Hydroxymethyl-2-methyl-propyl)-benzoylamino]-propionic acid ethyl ester The title compound is prepared by essentially following the procedures as described in Preparation 14, using 4-isobutyryl-benzoic acid methyl ester and beta-alanine ethyl ester hydrochloride as the starting materials. MS (ES): 306.2 [M+H]−.

Preparation 20

4'-tert-Butyl-biphenyl-4-ol

The title compound is prepared by essentially following the procedures as described in Preparation 1, Procedure B, using 4-tert-butyl phenyl boronic acid as starting material.

Preparation 21

4'-tert-Butyl-2,6-dimethyl-biphenyl-4-ol

The title compound is prepared by essentially following the procedures as described in Preparation 1, Procedure B, using 4-tert-butyl phenyl boronic acid and 3,5-dimethyl-phenol as starting materials.

Example 8 racemic 3-{4-[1-(4'-Trifluoromethyl-biphenyl-4-yloxymethyl)-heptyl]-benzoylamino}-propionic acid

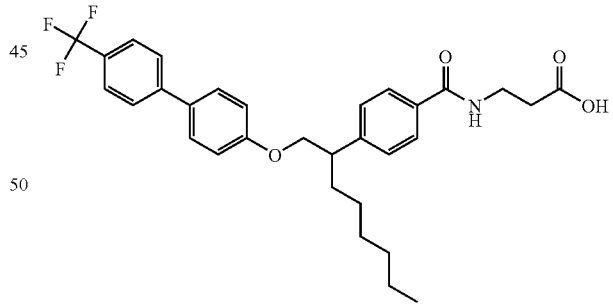

Step A. 3-{4-[1-(4'-Trifluoromethyl-biphenyl-4-yloxymethyl)-heptyl]-benzoylamino}-propionic acid methyl ester A solution of 4'-trifluoromethyl-biphenyl-4-ol (213 mg, 0.90 mmol) and 3-[4-(1-hydroxymethyl-heptyl)-benzoylamino]-propionic acid methyl ester (240 mg, 0.72 mmol) in anhydrous toluene (5 mL) is degassed and filled with nitrogen 3 times. Tributylphosphine (270 µL, 1.07 mmol) is added to the reaction mixture under nitrogen at 0° C., followed by addition of 1,1'-(azodicarbonyl)-dipiperidine (271 mg, 1.07 mmol). The reaction mixture is allowed to warm to room temperature and stirred overnight. The mixture is loaded on a silica gel column and purified using hexanes/ethyl acetate. Some racemic ester is hydrolyzed in the next step, and the remaining intermediate ester is sent to chiral chromatography for resolution (see Example 15, Step C). MS (ES): 554.2 [M+H]–.

Step B. racemic 3-{4-[1-(4'-Trifluoromethyl-biphenyl-4-yloxymethyl)-heptyl]-benzoylamino}-propionic acid 3-{4-[1-(4'-Trifluoromethyl-biphenyl-4-yloxymethyl)-heptyl]-benzoylamino}-propionic acid methyl ester (50 mg, 0.09 mmol) is dissolved in tetrahydrofuran (1 mL) and 5N sodium hydroxide (1 mL) is added. The reaction may be monitored by HPLC. After 3 h the reaction is neutralized with 5N HCl (1 mL) and diluted with diethyl ether and water. The two phases are separated, and the organic layer is washed, dried, and concentrated to provide the title compound. MS (ES): 540.3 [M+H]–.

Example 9 racemic 3-{4-[1-(4'-tert-Butyl-biphenyl-4-yloxymethyl)-heptyl]-benzoylamino}-propionic acid

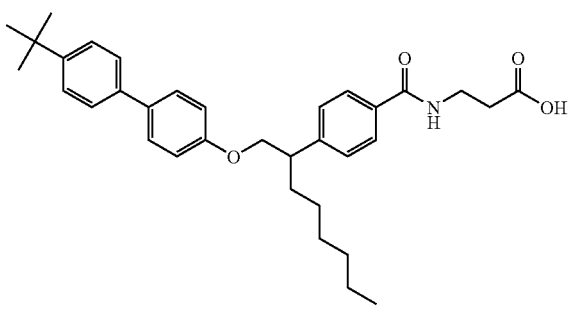

The title compound is prepared by essentially following the procedures as described in Example 8, using 4'-tert-butyl-biphenyl-4-ol and 3-[4-(1-hydroxymethyl-heptyl)-benzoylamino]-propionic acid methyl ester as starting materials. MS (ES): 528.3 [M+H]–.

Example 10 racemic 3-{4-[1-(4'-tert-Butyl-2,6-dimethyl-biphenyl-4-yloxymethyl)-3-methyl-butyl]-benzoylamino}-propionic acid

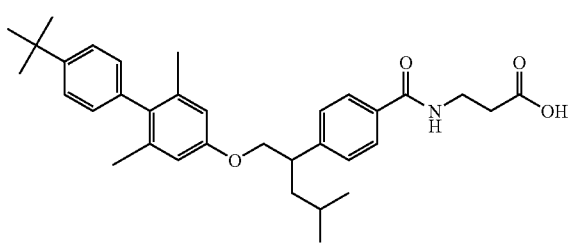

The title compound is prepared by essentially following the procedures as described in Example 8, using 4'-tert-butyl-2,6-dimethyl-biphenyl-4-ol and -[4-(1-hydroxymethyl-3-methyl-butyl)-benzoylamino]-propionic acid methyl ester as starting materials. MS (ES): 528.3 [M+H]–.

Example 11 racemic 3-{4-[1-(4'-tert-Butyl-biphenyl-4-yloxymethyl)-butyl]-benzoylamino}-propionic acid

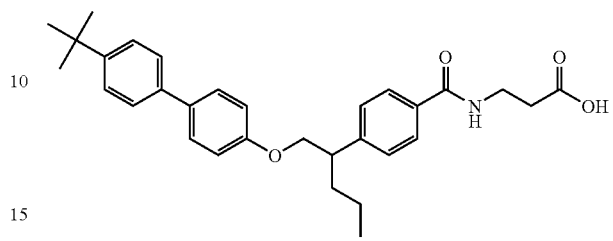

The title compound is prepared by essentially following the procedures as described in Example 8, using 4'-tert-butyl-biphenyl-4-ol and -[4-(1-hydroxymethyl-butyl)-benzoylamino]-propionic acid methyl ester as starting materials. MS (ES): 486.2 [M+H]–.

Example 12 racemic 3-{4-[1-(4'-Trifluoromethyl-biphenyl-4-yloxymethyl)-butyl]-benzoylamino}-propionic acid

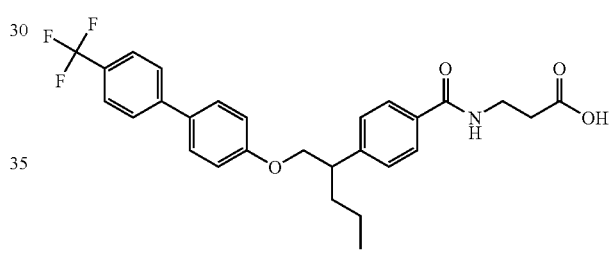

The title compound is prepared by essentially following the procedures as described in Example 8, using 4'-trifluoromethyl-biphenyl-4-ol and -[4-(1-hydroxymethyl-butyl)-benzoylamino]-propionic acid methyl ester as starting materials. MS (ES): 498.2 [M+H]–.

Example 13 racemic 3-{4-[1-(4'-tert-Butyl-biphenyl-4-yloxymethyl)-5,5,5-trifluoro-pentyl]-benzoylamino}-propionic acid

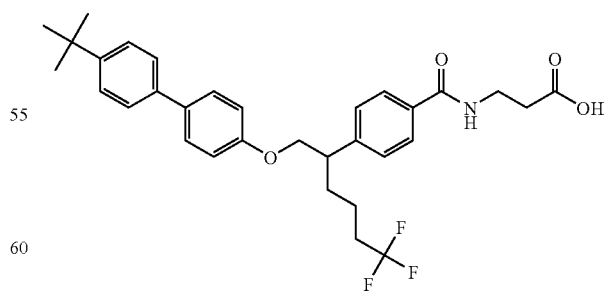

The title compound is prepared by essentially following the procedures as described in Example 8, using 4'-tert-butyl-biphenyl-4-ol and 3-[4-(5,5,5-trifluoro-1-hydroxymethyl-pentyl)-benzoylamino]-propionic acid methyl ester as starting materials. MS (ES): 554.2 [M+H]–.

Example 14 racemic 3-{4-[1-(2,6-Dimethyl-4'-trifluoromethyl-biphenyl-4-yloxymethyl)-3-methyl-butyl]-benzoylamino}-propionic acid

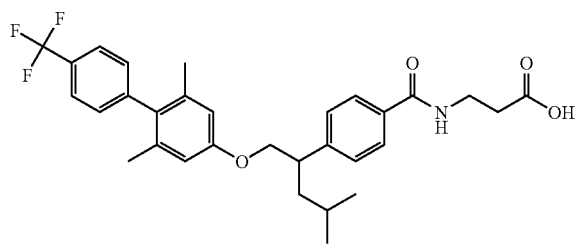

The title compound is prepared by essentially following the procedures as described in Example 8, using 2,6-dimethyl-4'-trifluoromethyl-biphenyl-4-ol and -[4-(1-hydroxymethyl-3-methyl-butyl)-benzoylamino]-propionic acid methyl ester as starting materials. MS (ES): 540.3 [M+H]−.

Example 15

3-{4-[1-(4'-Trifluoromethyl-biphenyl-4-yloxymethyl)-heptyl]-benzoylamino}-propionic acid, isomer 1

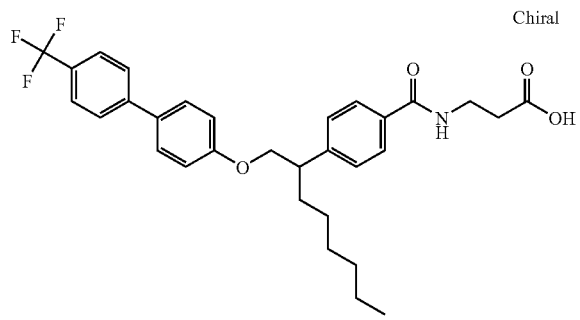

Step C. Chiral Separation

Racemic 3-{4-[1-(4'-trifluoromethyl-biphenyl-4-yloxymethyl)-heptyl]-benzoylamino}-propionic acid methyl ester is resolved on a Chiralpak AD-H column (4.6×150 mm) using isopropyl alcohol/heptane (30/70) as eluent. The appropriate fractions are concentrated to provide a pure enantiomer ester (isomer 1, 98.6% ee).

Step B. 3-{4-[1-(4'-Trifluoromethyl-biphenyl-4-yloxymethyl)-heptyl]-benzoylamino}-propionic acid, isomer 1

3-{4-[1-(4'-Trifluoromethyl-biphenyl-4-yloxymethyl)-heptyl]-benzoylamino}-propionic acid methyl ester, isomer 1 (250 mg, 0.45 mmol) is dissolved in tetrahydrofuran (1 mL) and 5N sodium hydroxide (1 mL) is added. The reaction may be monitored by HPLC. After a period of 3 hours, the reaction is neutralized with 5N HCl (1 mL) and diluted with diethyl ether and water. The two phases are separated, and the organic layer is washed, dried, and concentrated to provide the title compound. MS (ES): 540.3 [M+H]−.

Example 16

3-{4-[1-(4'-Trifluoromethyl-biphenyl-4-yloxymethyl)-heptyl]-benzoylamino}-propionic acid, isomer 2

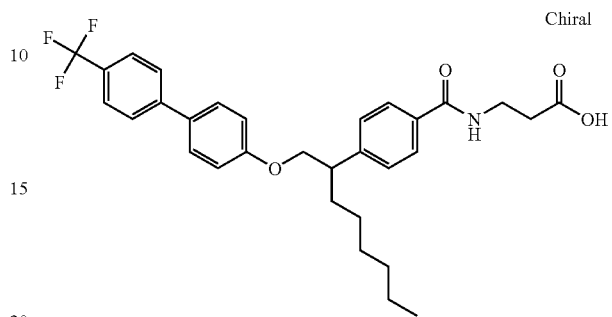

The title compound is prepared by essentially following the procedures as described in Example 15, using isomer 2 from the chiral separation of Step C. MS (ES): 540.3 [M+H]−.

Example 17

3-{4-[1-(4'-tert-Butyl-2,6-dimethyl-biphenyl-4-yloxymethyl)-3-methyl-butyl]-benzoylamino}-propionic acid, isomer 1

The title compound is prepared by essentially following the procedures as described in Example 15, using racemic 3-{4-[1-(4'-tert-butyl-2,6-dimethyl-biphenyl-4-yloxymethyl)-3-methyl-butyl]-benzoylamino}-propionic acid methyl ester. MS (ES): 528.3 [M+H]−.

Example 18

3-{4-[1-(4'-tert-Butyl-2,6-dimethyl-biphenyl-4-yloxymethyl)-3-methyl-butyl]-benzoylamino}-propionic acid isomer 2

The title compound is prepared by essentially following the procedures as described in Example 15, using isomer 2 from the chiral separation of Example 17. MS (ES): 528.3 [M+H]–.

Example 19

3-{4-[1-(2,6-Dimethyl-4'-trifluoromethyl-biphenyl-4-yloxymethyl)-3-methyl-butyl]-benzoylamino}-propionic acid, isomer 1

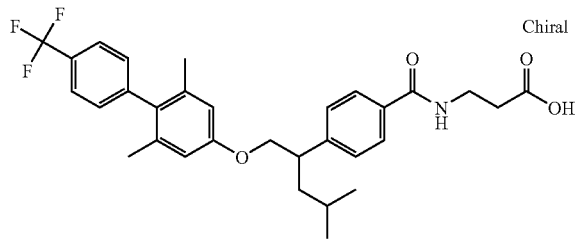

The title compound is prepared by essentially following the procedures as described in Example 15, using racemic 3-{4-[1-(2,6-dimethyl-4'-trifluoromethyl-biphenyl-4-yloxymethyl)-3-methyl-butyl]-benzoylamino}-propionic acid methyl ester. MS (ES): 540.3 [M+H]–.

Example 20

3-{4-[1-(2,6-Dimethyl-4'-trifluoromethyl-biphenyl-4-yloxymethyl)-3-methyl-butyl]-benzoylamino}-propionic acid, isomer 2

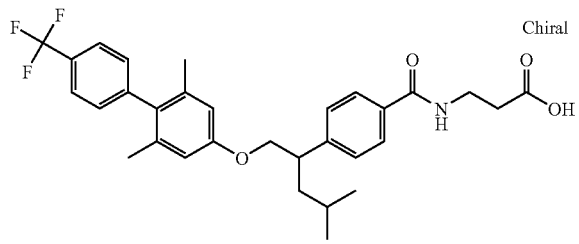

The title compound is prepared by essentially following the procedures as described in Example 15, using isomer 2 from the chiral separation of Example 19. MS (ES): 540.3 [M+H]–.

Example 21 racemic 3-{4-[1-(2,6-Dimethyl-4'-trifluoromethyl-biphenyl-4-yloxymethyl)-2-methyl-propyl]-benzoylamino}-propionic acid

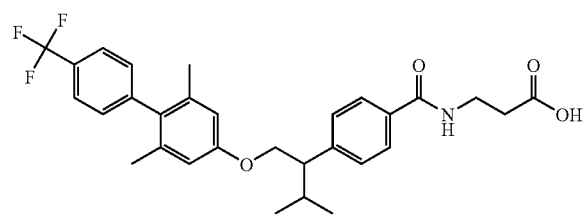

Step A. 3-{4-[1-(4-Bromo-3,5-dimethyl-phenoxymethyl)-2-methyl-propyl]-benzoylamino}-propionic acid ethyl ester A solution of 4-bromo-3,5-dimethyl-phenol (818 mg, 4.07 mmol) and 3-[4-(1-hydroxymethyl-2-methyl-propyl)-benzoylamino]-propionic acid ethyl ester (1.0 g, 3.26 mmol) in anhydrous toluene (15 mL) is degassed and filled with nitrogen 3 times. Tributylphosphine (1.21 mL, 4.89 mmol) is added to the reaction mixture under nitrogen at 0° C., followed by addition of 1,1'-(azodicarbonyl)-dipiperidine (1.23 g, 4.89 mmol). The reaction mixture is allowed to warm to room temperature and stirred overnight. The mixture is loaded on a silica gel column and purified using hexanes/ethyl acetate. MS (ES): 488.2 [M+H]–.

Step B. racemic 3-{4-[1-(2,6-Dimethyl-4'-trifluoromethyl-biphenyl-4-yloxymethyl)-2-methyl-propyl]-benzoylamino}-propionic acid ethyl ester To a solution of 3-{4-[1-(4-bromo-3,5-dimethyl-phenoxymethyl)-2-methyl-propyl]-benzoylamino}-propionic acid ethyl ester (400 mg, 0.82 mmol) in toluene:water (1:1) (4 mL) is added tetrakis(triphenylphosphine) palladium (0) (47 mg, 0.04 mmol) and 4-trifluoromethyl phenylboronic acid (311 mg, 1.63 mmol). The reaction is purged with nitrogen and heated to reflux and potassium fluoride (95 mg, 1.63 mmol) is added. The reaction is monitored by HPLC. After 16 h the reaction is allowed to cool to room temperature. The reaction is diluted with ethyl acetate and then Celite® is added, followed by water. This mixture is then filtered through a pad of Celite®. The solution is poured into a separatory funnel and the organic layer is washed with 0.1N sodium hydroxide, water, and brine. The organic layer is dried over anhydrous sodium sulfate and concentrated. The racemic 3-{4-[1-(2,6-dimethyl-4'-trifluoromethyl-biphenyl-4-yloxymethyl)-2-methyl-propyl]-benzoylamino}-propionic acid ethyl ester (400 mg, 0.72 mmol) is purified by flash column chromatography using hexanes/ethyl acetate, and some of the intermediate ester is sent to chiral chromatography for resolution (see Example 25, Step D).

Step C. racemic 3-{4-[1-(2,6-Dimethyl-4'-trifluoromethyl-biphenyl-4-yloxymethyl)-2-methyl-propyl]-benzoylamino}-propionic acid Racemic 3-{4-[1-(2,6-dimethyl-4'-trifluoromethyl-biphenyl-4-yloxymethyl)-2-methyl-propyl]-benzoylamino}-propionic acid ethyl ester (50 mg, 0.09 mmol) is dissolved in tetrahydrofuran (1 mL) and 5N sodium hydroxide (1 mL) is added. The reaction may be monitored by HPLC. After a period of 3 h, the reaction is neutralized with 5N HCl (1 mL), and diluted with diethyl ether and water. The two phases are separated, and the organic layer is washed, dried, and concentrated to provide the title compound without further purification. MS (ES): 526.2 [M+H]–.

Example 22 racemic 3-{4-[1-(4'-tert-Butyl-2,6-dimethyl-biphenyl-4-yloxymethyl)-2-methyl-propyl]-benzoylamino}-propionic acid

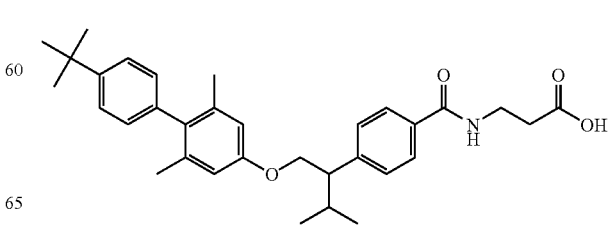

The title compound is prepared by essentially following the procedures as described in Example 21, using 3-{4-[1-(4-bromo-3,5-dimethyl-phenoxymethyl)-2-methyl-propyl]-benzoylamino}-propionic acid ethyl ester and 4-tert-butyl phenyl boronic acid as starting materials. MS (ES): 514.2 [M+H]–.

Example 23 racemic 3-(4-{1-[6-(4-Trifluoromethyl-phenyl)-pyridin-3-yloxymethyl]-butyl}-benzoylamino)-propionic acid

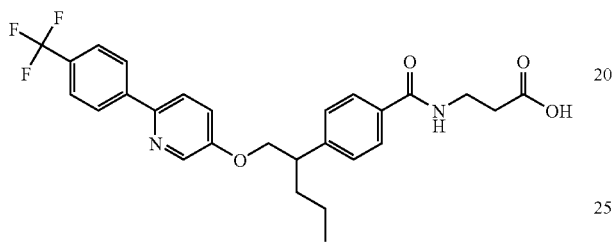

The title compound is prepared by essentially following the procedures as described in Example 21, using 3-[4-(1-hydroxymethyl-butyl)-benzoylamino]-propionic acid methyl ester and 6-chloro-pyridin-3-ol as starting materials in Step A, followed by 4-trifluoromethyl phenyl boronic acid in Step B. MS (ES): 499.2 [M+H]–.

Example 24 racemic 3-{4-[1-(2,6-Dimethyl-4'-trifluoromethyl-biphenyl-4-yloxymethyl)-4,4,4-trifluoro-butyl]-benzoylamino}-propionic acid

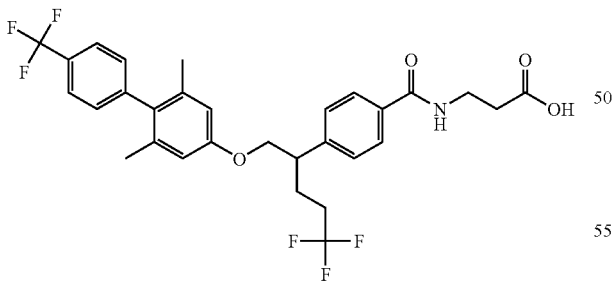

The title compound is prepared by essentially following the procedures as described in Example 21, using 3-[4-(4,4,4-trifluoro-1-hydroxymethyl-butyl)-benzoylamino]-propionic acid methyl ester as starting material and 4-iodo-3,5-dimethyl-phenol in place of 4-bromo-3,5-dimethyl-phenol. MS (ES): 580.2 [M+H]–.

Example 25

3-{4-[1-(2,6-Dimethyl-4'-trifluoromethyl-biphenyl-4-yloxymethyl)-2-methyl-propyl]-benzoylamino}-propionic acid isomer 1

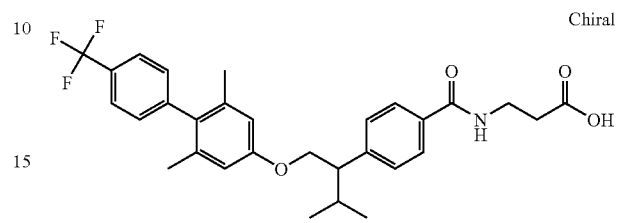

Step D. Chiral Separation

The racemic 3-{4-[1-(2,6-dimethyl-4'-trifluoromethyl-biphenyl-4-yloxymethyl)-2-methyl-propyl]-benzoylamino}-propionic acid ethyl ester is resolved on a Chiralpak AD-H column (4.6×150 mm) using isopropyl alcohol/heptane (30/70) as eluent. The appropriate fractions were concentrated to provide a pure enantiomer ester (isomer 1, >99% ee).

Step E. 3-{4-[1-(4'-Trifluoromethyl-biphenyl-4-yloxymethyl)-heptyl]-benzoylamino}-propionic acid, isomer 1

3-{4-[1-(2,6-Dimethyl-4'-trifluoromethyl-biphenyl-4-yloxymethyl)-2-methyl-propyl]-benzoylamino}-propionic acid ethyl ester, isomer 1 (250 mg, 0.462 mmol) is dissolved in tetrahydrofuran (1 mL) and 5N sodium hydroxide (1 mL) is added. The reaction may be monitored by HPLC. After a period of 3 h, the reaction is neutralized with 5N HCl (1 mL) and diluted with diethyl ether and water. The two phases are separated, and the organic layer is washed, dried, and concentrated. The title compound is provided without further purification. MS (ES): 526.2 [M+H]–.

Example 26

3-{4-[1-(2,6-Dimethyl-4'-trifluoromethyl-biphenyl-4-yloxymethyl)-2-methyl-propyl]-benzoylamino}-propionic acid, isomer 2

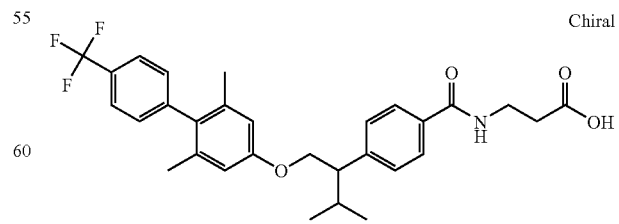

The title compound is prepared by essentially following the procedures as described in Example 25, using isomer 2 from the chiral separation. MS (ES): 526.2 [M+H]–.

Example 27

3-{4-[1-(4'-tert-Butyl-2,6-dimethyl-biphenyl-4-yloxymethyl)-2-methyl-propyl]-benzoylamino}-propionic acid, isomer 1

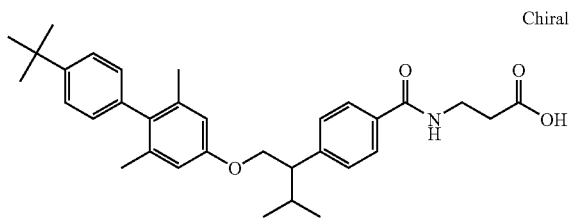

The title compound is prepared by essentially following the procedures as described in Example 25, using racemic 3-{4-[1-(4'-tert-butyl-2,6-dimethyl-biphenyl-4-yloxymethyl)-2-methyl-propyl]-benzoylamino}-propionic acid ethyl ester. MS (ES): 514.2 [M+H]−.

Example 28

33-{4-[1-(4'-tert-Butyl-2,6-dimethyl-biphenyl-4-yloxymethyl)-2-methyl-propyl]-benzoylamino}-propionic acid, isomer 2

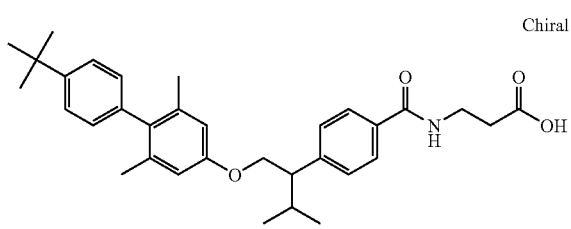

The title compound is prepared by essentially following the procedures as described in Example 25, using isomer 2 from the chiral separation of Example 27. MS (ES): 514.2 [M+H]−.

Example 29

3-{4-[1-(2,6-Dimethyl-4'-trifluoromethyl-biphenyl-4-yloxymethyl)-4,4,4-trifluoro-butyl]-benzoylamino}-propionic acid, isomer 1

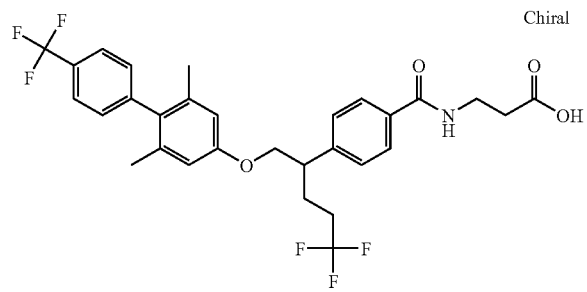

The title compound is prepared by essentially following the procedures as described in Example 25, using racemic 3-{4-[1-(2,6-dimethyl-4'-trifluoromethyl-biphenyl-4-yloxymethyl)-4,4,4-trifluoro-butyl]-benzoylamino}-propionic acid ethyl ester. MS (ES): 580.3 [M+H]−.

Example 30

3-{4-[1-(2,6-Dimethyl-4'-trifluoromethyl-biphenyl-4-yloxymethyl)-4,4,4-trifluoro-butyl]-benzoylamino}-propionic acid, isomer 2

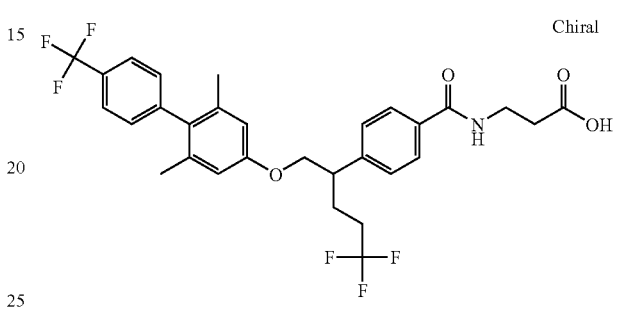

The title compound is prepared by essentially following the procedures as described in Example 25, using isomer 2 from the chiral separation of Example 29. MS (ES): 580.3 [M+H]−.

The compound of Formula I is preferably formulated in a unit dosage form prior to administration. Therefore, yet another embodiment of the present invention is a pharmaceutical composition comprising a compound of Formula I and one or more pharmaceutically acceptable carriers, diluents or excipients. In such form, the preparation is subdivided into suitably sized unit doses containing appropriate quantities of the active components, e.g., an effective amount to achieve the desired purpose. Such pharmaceutical compositions and processes for preparing same are well known in the art. See, e.g. REMINGTON: THE SCIENCE AND PRACTICE OF PHARMACY (A. Gennaro, et al., eds., 19$^{th}$ ed., Mack Publishing Co., 1995). The particular dosage of a compound of formula (I) or a pharmaceutically acceptable salt thereof required to constitute an effective amount according to this invention will depend upon the particular circumstances of the conditions to be treated. Preferably the compound is administered orally. The quantity of the inventive active composition in a unit dose of preparation may be generally varied or adjusted from about 0.01 milligrams to about 1,000 milligrams, preferably from about 0.01 to about 950 milligrams, more preferably from about 0.01 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art. Generally, the human oral dosage form containing the active ingredients can be administered 1 or 2 times per day. Considerations such as dosage, route of administration, and frequency of dosing are best decided by the attending physician.

There is increasing evidence that glucagon plays an important role in glucose homeostasis. Compounds of Formula I are effective as antagonists or inverse agonists of the glucagon receptor, and thus inhibit the activity of the glucagon receptor. More particularly, these compounds are selective antagonists or inverse agonists of the glucagon receptor. As selective antagonists or inverse agonists, the compounds of Formula I are useful in the treatment of diseases, disorders, or conditions responsive to the inactivation of the glucagon receptor, including but not limited to diabetic and other glucagon related disorders. It is expected that selective antagonists or inverse agonists of the glucagon receptor will lower plasma glucose levels and thus prevent or treat diabetic and other glucagon related metabolic disorders.

Pharmacological Methods

In the following section binding assays as well as functional assays useful for evaluating the efficiency of the compounds of the invention are described. Binding of compounds to the glucagon receptor may be determined in a competition binding assay using the cloned human glucagon receptor, and selectivity against the hGlp1 receptor. Antagonism may be determined as the ability of the compounds to inhibit the amount of cAMP formed in the assay in the presence of 5 nM glucagon.

Glucagon Receptor (hGlucR) Binding Assay

The receptor binding assay uses cloned human glucagon receptor (Lok S, Kuijper J L, Jelinek L J, Kramer J M, Whitmore T E, Sprecher C A, Mathews S, Grant F J, Biggs S H, Rosenberg G B, et al. Gene 140 (2), 203-209 (1994)) isolated from 293HEK membranes. The hGlucR cDNA is subcloned into the expression plasmid phD (Trans-activated expression of fully gamma-carboxylated recombinant human protein C, an antithrombotic factor. Grinnell, B. W., Berg, D. T., Walls, J. and Yan, S. B. Bio/Technology 5: 1189-1192 (1987)). This plasmid DNA is transfected into 293 HEK cells and selected with 200 µg/mL Hygromycin.

Crude plasma membranes are prepared using cells from suspension culture. The cells are lysed on ice in hypotonic buffer containing 25 mM Tris HCL, pH 7.5, 1 mM MgCl2, DNAseI, 20 u/mL, and Roche Complete Inhibitors-without EDTA. The cell suspension is homogenized with a glass dounce homogenizer using a Teflon pestle for 25 strokes. The homogenate is centrifuged at 4 degrees C. at 1800×g for 15 mins. The supernate is collected and the pellet is resuspended in hypotonic buffer and rehomogenized. The mixture is centrifuged at 1800×g for 15 mins. The second supernate is combined with the first supernate. The combined supernates are recentrifuged at 1800×g for 15 mins to clarify. The clarified supernate is transferred to high speed tubes and centrifuged at 25000×g for 30 minutes at 4 degrees C. The membrane pellet is resuspended in homogenization buffer and stored as frozen aliquots at −80 degree C. freezer until needed.

Glucagon is radioiodinated by I-125-lactoperoxidase procedure and purified by reversed phase HPLC at Perkin-Elmer/ NEN (NEX207). The specific activity is 2200 Ci/mmol. Kd determination is performed by homologous competition instead of saturation binding due to high propanol content in the I-125 glucagon material. The Kd is estimated to be 3 nM and is used to calculate Ki values for all compounds tested.

The binding assays are carried out using a Scintillation Proximity Assay (Amersham) with WGA beads previously blocked with 1% fatty acid free BSA (ICN). The binding buffer contains 25 mM Hepes, pH 7.4, 2.5 mM CaCl2, 1 mM MgCl2, 0.1% fatty acid free BSA, (ICN), 0.003% tween-20, and Roche Complete Inhibitors without EDTA. Glucagon is dissolved in 0.01 N HCl at 1 mg/mL and immediately frozen at −80 degrees C. in 30 µl aliquots. The glucagon aliquot is diluted and used in binding assays within an hour. Test compounds are dissolved in DMSO and serially diluted in DMSO. 10 ul diluted compounds or DMSO is transferred into Corning 3632, opaque clear bottom assay plates containing 90 µl assay binding buffer or cold glucagon (NSB at 1 µM final). 50 µl of I-125 glucagon (0.15 nM final in reaction), 50 µl of membranes (300 µg/well), and 40 µl of WGA beads (150 mgs/well) are added, covered, and mixed end over end. Plates are read with a MicroBeta after 14 hours of settling time at room temp.

Results are calculated as a percent of specific I-125-glucagon binding in the presence of compound. The absolute EC50 dose of compound is derived by non-linear regression of percent specific binding of I-125-glucagon vs. the dose of compound added. The EC50 dose is converted to Ki using the Cheng-Prusoff equation (Cheng Y., Prusoff W. H., Biochem. Pharmacol. 22, 3099-3108, 1973).

Glucagon-Like—Peptide 1 (Glp1-R) Receptor Binding Assay

The receptor binding assay uses cloned human glucagon-like peptide 1 receptor (hGlp1-R) (Graziano M P, Hey P J, Borkowski D, Chicchi G G, Strader C D, Biochem Biophys Res Commun. 1993 Oct. 15; 196(1):141-6) isolated from 293HEK membranes. The hGlp1-R cDNA is subcloned into the expression plasmid phD (Trans-activated expression of fully gamma-carboxylated recombinant human protein C, an antithrombotic factor. Grinnell, B. W., Berg, D. T., Walls, J. and Yan, S. B. Bio/Technology 5: 1189-1192 (1987)). This plasmid DNA is transfected into 293 HEK cells and selected with 200 µg/mL Hygromycin.

Crude plasma membrane is prepared using cells from suspension culture. The cells are lysed on ice in hypotonic buffer containing 25 mM Tris HCl, pH 7.5, 1 mM MgCl2, DNAse, 20 µ/mL, and Roche Complete Inhibitors without EDTA. The cell suspension is homogenized with a glass dounce homogenizer using a Teflon pestle for 25 strokes. The homogenate is centrifuged at 4 degrees C. at 1800×g for 15 mins. The supernate is collected and the pellet is resuspended in hypotonic buffer and rehomogenized. The mixture is centrifuged at 1800×g for 15 mins. The second supernate is combined with the first supernate. The combined supernates are recentrifuged at 1800×g for 15 mins to clarify. The clarified supernate is transferred to high speed tubes and centrifuged at 25000×g for 30 minutes at 4 degrees C. The membrane pellet is resuspended in homogenization buffer and stored as frozen aliquots in −80 degree C. freezer until use.

Glucagaon-like peptide 1 (Glp-1) is radioiodinated by the I-125-lactoperoxidase procedure and purified by reversed phase HPLC at Perkin-Elmer/NEN (NEX308). The specific activity is 2200 Ci/mmol. Kd determination is performed by homologous competition instead of saturation binding due to high propanol content in the I-125 Glp-1 material. The Kd is estimated to be 3 nM and is used to calculate Ki values for all compounds tested.

The binding assays are carried out using a Scintillation Proximity Assay (Amersham) with wheat germ agglutinin (WGA) beads previously blocked with 1% fatty acid free BSA (ICN). The binding buffer contains 25 mM Hepes, pH 7.4, 2.5 mM CaCl2, 1 mM MgCl2, 0.1% fatty acid free BSA, (ICN), 0.003% tween-20, and Roche Complete Inhibitors without EDTA. Glucagon-like peptide 1 is dissolved in PBS at 1 mg/mL and immediately frozen at −80 degrees C. in 30 µl aliquots. The glucagon-like peptide aliquot is diluted and used in binding assays within an hour. Test compounds are dissolved in DMSO and serially diluted in DMSO. 10 µl diluted compounds or DMSO is transferred into Corning 3632, opaque clear bottom assay plates containing 90 µl assay binding buffer or cold glucagon-like peptide 1 (NSB at 1 µM final). 50 µl of I-125 glucagon-like peptide 1 (0.15 nM final in reaction), 50 µl of membranes (600 µg/well), and 40 µl of WGA beads (150 µgs/well) are added, covered, and mixed end over end. Plates are read with a MicroBeta after 14 hours of settling time at room temp.

Results are calculated as a percent of specific I-125-glucagon-like peptide 1 binding in the presence of compound. The absolute EC50 dose of compound is derived by non-linear regression of percent specific binding of I-125-glucagon-like peptide 1 vs. the dose of compound added. The EC50 dose is converted to Ki using the Cheng-Prusoff equation (Cheng Y., Prusoff W. H., Biochem. Pharmacol. 22, 3099-3108, 1973).

Glucagon-Stimulated cAMP Functional Antagonist Assay

The cAMP functional assay uses the same cloned human glucagon receptor cell line isolated for the hGlucR binding assay described above. Cells are stimulated with a mixture of an EC80 dose of glucagon in the presence of compound. The cAMP generated within the cell is quantitated using an Amplified Luminescent Proximity Homogeneous Assay, Alpha Screen, from Perkin Elmer (6760625R). Briefly, cAMP within the cell competes for binding of biotinylated cAMP from the kit to a coated anti-cAMP antibody Acceptor bead and a strepavidin coated Donor bead. As the cAMP level within the cell increases, a disruption of the Acceptor bead-biotinlyated cAMP-Donor bead complex occurs and decreases the signal.

Glucagon is dissolved in 0.01 N HCl at 1 mg/mL and immediately frozen at −80 degrees C. in 30 ul aliquots. The glucagon aliquot is diluted and used in the functional assay within an hour. Cells are harvested from sub-confluent tissue culture dishes with Enzyme-Free Cell Dissociation Solution, (Specialty Media 5-004-B). The cells are pelleted at low speed and washed 3 times with assay buffer [25 mM Hepes in HBSS-with Mg and Ca (GIBCO, 14025-092) with 0.1% Fatty Acid Free BSA (ICN)] then diluted to a final concentration of 250,000 cells per mL. Compounds are serially diluted into DMSO then diluted into assay buffer with a 3× concentration of glucagon and 3% DMSO. The EC80 of glucagon is pre-determined from a full glucagon dose response and represents the dose at which glucagons produces an 80% of the maximal glucagon response. A mixture of biotinylated cAMP (1 unit/well final) from the Alpha Screen Kit and 3× IBMX (1500 µM) is prepared in Assay Buffer.

The functional assay is performed in 96 well, low-volume, white, poylstyrene Costar Plates (3688). The biotinylated cAMP/IBMX mixture, 0.02 mLs, is placed into each well, followed by addition of 0.02 mLs of glucagon dose response, cAMP standard curve, or compound/glucagon mixtures. The reaction is started by addition of 0.02 mLs of cells (5000/well final). After 60 minutes at room temperature, the reaction is stopped by the addition of 0.03 mLs of Lysis Buffer [10 mM Hepes, pH 7.4, 1% NP40, and 0.01% fatty acid free BSA (ICN) containing 1 unit each/well of Acceptor and Donor beads from the Alpha Screen Kit]. Lysis Buffer addition is performed under a green light to prevent bleaching of the detection beads. The plates are wrapped in foil and left to equilibrate overnight at room temperature. The plates are read on a Packard Fusion™-α Instrument.

Alpha screen units are converted to pmoles cAMP generated per well based upon the cAMP standard curve. The pmoles cAMP produced in the presence of compound are converted to % of a maximal response with the EC80 dose of glucagon alone. With each experiment, the dose of glucagon needed to produce a 50% response of pmoles cAMP is determined. This EC50 dose is used to normalize results to a Kb using a modified Cheng-Prusoff equation (Cheng Y., Prusoff W. H., Biochem. Pharmacol. 22, 3099-3108, 1973), where Kb=(EC50 compound)/[1+(pM glucagon used/EC50 in pM for glucagon dose response)].

The compounds according to the invention preferably have a $K_i$ value of no greater than 50 µM as determined by the Glucagon Receptor (hGlucR) Binding Assay disclosed herein. More preferably, the compounds according to the invention have a Ki value of less than 5 µM, preferably of less than 500 nM and even more preferred of less than 100 nM as determined by the Glucagon Receptor (hGlucR) Binding Assay disclosed herein. Generally, the compounds according to the invention show a higher affinity for the glucagon receptor compared to the GLP-1 receptor, and preferably have a higher binding affinity to the glucagon receptor than to the GLP-1 receptor. All of the examples provided herein have a Ki value of less than 5 µM.

The results are given below for the indicated compound.

TABLE 1

| Example | Ki (nM) |
|---|---|
| [structure] | 87 |
| [structure] | 61 |

From the above description, one skilled in the art can ascertain the essential characteristics of the present invention, and without departing from the spirit and scope thereof, can make various changes and modifications of the invention to adapt it to various usages and conditions. Thus, other embodiments are also within the claims.

What is claimed is:

1. A compound structurally represented by Formula I

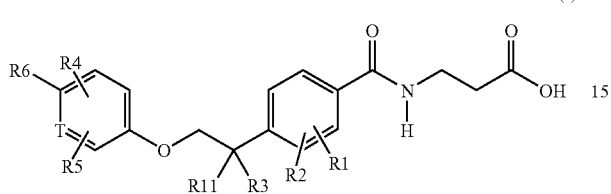

(I)

or a pharmaceutically acceptable salt thereof wherein:
T is carbon or nitrogen;
R1 and R2 are independently —H or -halogen;
R3 is
—($C_1$-$C_8$)alkyl (optionally substituted with 1 to 3 halogens), —($C_2$-$C_7$)alkenyl (optionally substituted with 1 to 3 halogens), —($C_3$-$C_7$)cycloalkyl,
—($C_1$-$C_6$)alkyl-($C_3$-$C_7$)cycloalkyl, or
—($C_3$-$C_7$)cycloalkyl-($C_1$-$C_6$)alkyl (optionally substituted with 1 to 3 halogens);
R4 and R5 are independently
—H, -halogen, -hydroxy, hydroxymethyl, —CN, —($C_1$-$C_7$)alkoxy,
—($C_2$-$C_7$)alkenyl, or —($C_1$-$C_6$)alkyl (optionally substituted with 1 to 3 halogens);
R6 is

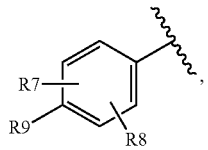

wherein the zig-zag mark shows the point of attachment to the parent molecule;
R7 and R8 are independently
—H, -halogen, —($C_1$-$C_6$)alkyl (optionally substituted with 1 to 3 halogens),
—($C_1$-$C_6$)alkoxy, —($C_3$-$C_7$)cycloalkyl, —C(O)R10, —COOR10, —OC(O)R10,
—OS(O)$_2$R10, —SR10, —S(O)R10, —S(O)$_2$R10, or —O($C_2$-$C_7$)alkenyl;
R9 is independently
—H, halogen, —CN, —($C_3$-$C_7$)cycloalkyl, —C(O)R10, —COOR10, —OC(O)R10,
—OS(O)$_2$R10, —SR10, —S(O)R10, —S(O)$_2$R10, or —O($C_2$-$C_7$)alkenyl, —($C_1$-$C_3$)alkoxy (optionally substituted with 1 to 3 halogens), or —($C_1$-$C_6$)alkyl (optionally substituted with 1 to 3 halogens);
R10 is independently at each occurrence
-hydrogen, or —($C_1$-$C_6$)alkyl (optionally substituted with 1 to 3 halogens); and
R11 is independently
—H, —($C_1$-$C_8$)alkyl (optionally substituted with 1 to 3 halogens), or —($C_2$-$C_7$)alkenyl (optionally substituted with 1 to 3 halogens); provided however that if R11 is —($C_1$-$C_8$)alkyl (optionally substituted with 1 to 3 halogens), or —($C_2$-$C_7$)alkenyl (optionally substituted with 1 to 3 halogens) then R3 is the same moiety as R11;
or R11 and R3 together with the carbon to which they are attached form a cycloalkyl ring having five carbons (wherein optionally the cycloalkyl ring having five carbons may contain one double bond).

2. A compound or salt of claim 1 wherein
T is carbon or nitrogen;
R1 and R2 are —H;
R3 is
—($C_1$-$C_8$)alkyl (optionally substituted with 1 to 3 halogens), —($C_2$-$C_7$)alkenyl (optionally substituted with 1 to 3 halogens), —($C_3$-$C_6$)cycloalkyl,
—($C_1$-$C_6$)alkyl-($C_3$-$C_6$)cycloalkyl, or —($C_3$-$C_6$)cycloalkyl-($C_1$-$C_6$)alkyl (optionally substituted with 1 to 3 halogens);
R4 and R5 are independently
—H, -halogen, or —($C_1$-$C_6$)alkyl (optionally substituted with 1 to 3 halogens);
R6 is

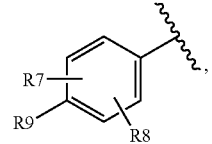

wherein the zig-zag mark shows the point of attachment to the parent molecule;
R7 and R8 are independently
—H, -halogen, —($C_1$-$C_3$)alkyl (optionally substituted with 1 to 3 halogens), —($C_1$-$C_3$)alkoxy;
R9 is independently
—H, halogen, or —($C_1$-$C_6$)alkyl (optionally substituted with 1 to 3 halogens); and
R11 is independently
—H, —($C_1$-$C_8$)alkyl (optionally substituted with 1 to 3 halogens), or —($C_2$-$C_7$)alkenyl (optionally substituted with 1 to 3 halogens); provided however that if R11 is —($C_1$-$C_8$)alkyl (optionally substituted with 1 to 3 halogens), or —($C_2$-$C_7$)alkenyl (optionally substituted with 1 to 3 halogens) then R3 is the same moiety as R11;
or R11 and R3 together with the carbon to which they are attached form a cycloalkyl ring having five carbons (wherein optionally the cycloalkyl ring having five carbons may contain one double bond).

3. A compound or salt of claim 1 wherein
R1 and R2 are —H;
R3 is
—($C_1$-$C_8$)alkyl (optionally substituted with 1 to 3 halogens), —($C_2$-$C_3$)alkenyl (optionally substituted with 1 to 3 halogens), —($C_3$-$C_6$)cycloalkyl,
—($C_1$-$C_6$)alkyl-($C_3$-$C_6$)cycloalkyl, or —($C_3$-$C_6$)cycloalkyl-($C_1$-$C_6$)alkyl (optionally substituted with 1 to 3 halogens);
R4 and R5 are independently
—H, -halogen, or —$CH_3$ (optionally substituted with 1 to 3 halogens);

R6 is

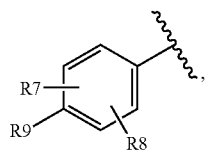

wherein the zig-zag mark shows the point of attachment to the parent molecule;
R7 and R8 are independently —H, or -halogen;
R9 is independently —($C_1$-$C_6$)alkyl (optionally substituted with 1 to 3 halogens); and
R11 is independently
- —H, —($C_1$-$C_3$)alkyl (optionally substituted with 1 to 3 halogens), or —($C_2$-$C_3$)alkenyl (optionally substituted with 1 to 3 halogens); provided however that if R11 is —($C_1$-$C_3$)alkyl (optionally substituted with 1 to 3 halogens), or —($C_2$-$C_3$)alkenyl (optionally substituted with 1 to 3 halogens) then R3 is the same moiety as R11;
- or R11 and R3 together with the carbon to which they are attached form a cycloalkyl ring having five carbons (wherein optionally the cycloalkyl ring having five carbons may contain one double bond).

4. A compound or salt of claim 1 wherein
T is carbon;
R1 and R2 are —H; R3 is —($C_1$-$C_8$)alkyl (optionally substituted with 1 to 3 halogens), —($C_3$-$C_6$)cycloalkyl, —($C_1$-$C_6$)alkyl-($C_3$-$C_6$)cycloalkyl, or —($C_3$-$C_6$)cycloalkyl-($C_1$-$C_6$)alkyl (optionally substituted with 1 to 3 halogens); R4 and R5 are —$CH_3$ (optionally substituted with 1 to 3 halogens) and each occupies a position ortho to R6 on the phenyl ring to which R6 is attached;

R6 is

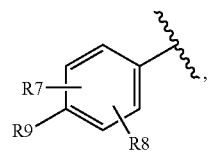

wherein the zig-zag mark shows the point of attachment to the parent molecule;
R7 and R8 are —H; and R9 is independently —($C_1$-$C_6$)alkyl (optionally substituted with 1 to 3 halogens); and R11 is —H.

5. A compound or salt of claim 1 wherein
R1 and R2 are independently hydrogen or halogen; R3 is methyl, ethyl, propyl, 2-propenyl, isopropyl, butyl, pentyl, hexyl, heptyl, octyl, 3,3-dimethylbutyl, 2-methylpropyl, 3-methyl-butyl, tertbutyl, 4-methylpentyl, 2,2-dimethylpropyl, 3-trifluoropropyl, 4-trifluorobutyl, cyclopropyl, cyclobutyl, cyclopentyl, or cyclohexyl; R4 and R5 are independently hydrogen, methyl, ethyl, tertbutyl, cyclohexyl, pentyl, isopropoxy, chloro, fluoro, bromo, hydroxy, trifluoromethyl, —CN, methoxy, hydroxymethyl, 4-methylpentyloxy, or pentyloxy; R7 and R8 are independently hydrogen, fluoro, chloro, methyl, ethyl, pentyl, isopropyl, tertbutyl, trifluoromethyl, acetyl, 2-methylpropyl, methoxy, cyclohexyl, or trifluoromethoxy; R9 is hydrogen, bromo, fluoro, methyl, tertbutyl, trifluoromethyl, or isopropyl; and R11 is —H, methyl, ethyl, propyl, or 2-propenyl, (provided that when R11 is methyl, ethyl, propyl, or 2-propenyl, then R3 is the same moiety as R11), or R11 and R3 together with the carbon to which they are attached form cyclopentyl, or cyclopent-3-enyl.

6. The compound of claim 1, selected from the group consisting of formulae X1 to X14, and X19 to X22;

| Formula Number | Structure |
|---|---|
| X1 | 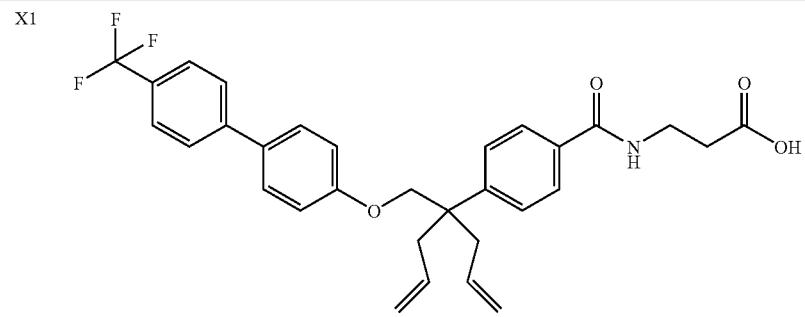 |
| X2 | 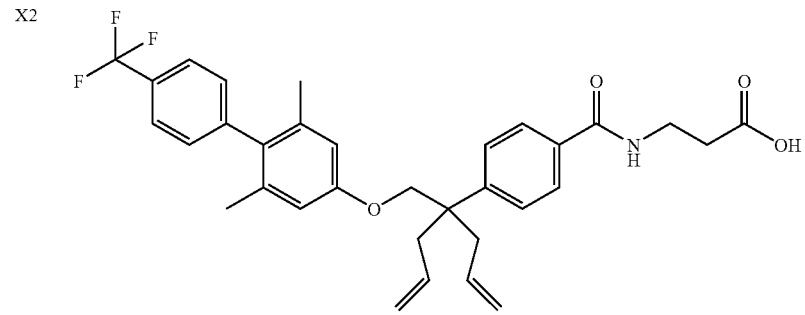 |

-continued
| Formula Number | Structure |
|---|---|
| X3 | 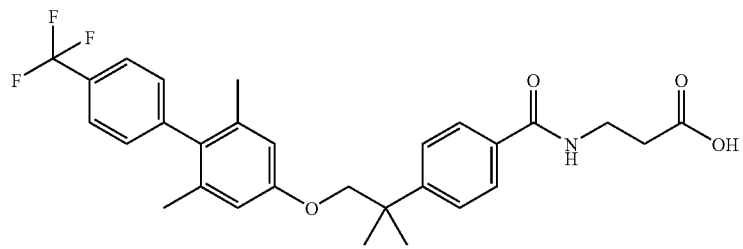 |
| X4 | 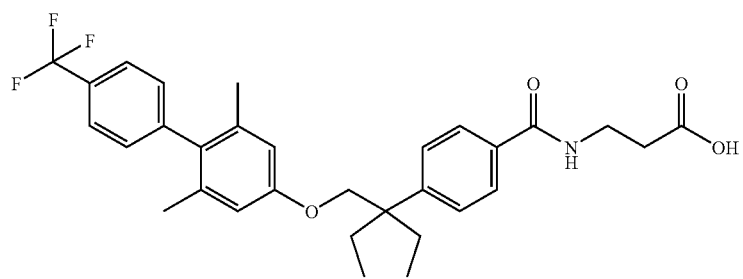 |
| X5 | 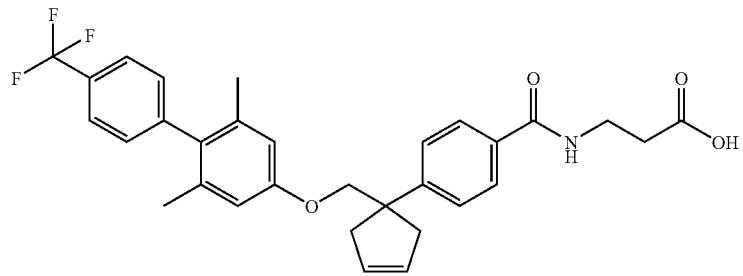 |
| X6 | 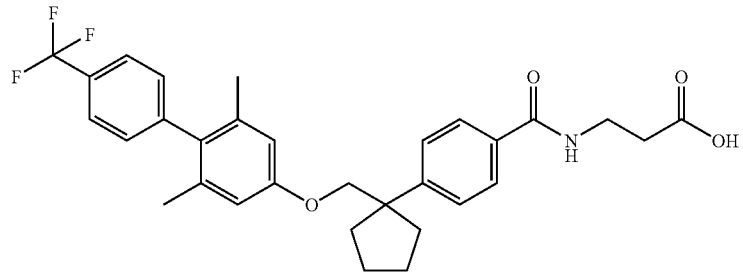 |
| X7 | 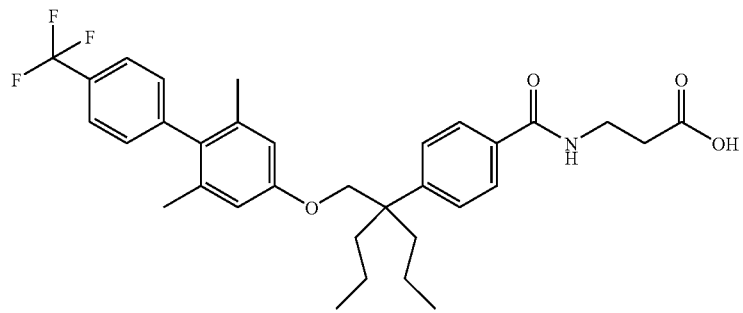 |

-continued
| Formula Number | Structure |
|---|---|
| X8 | 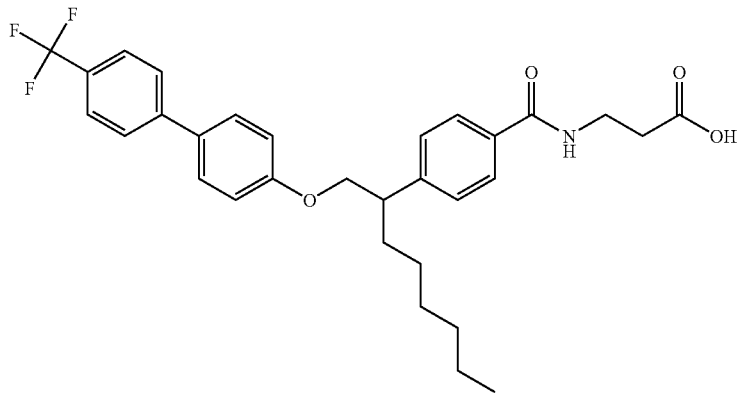 |
| X9 | 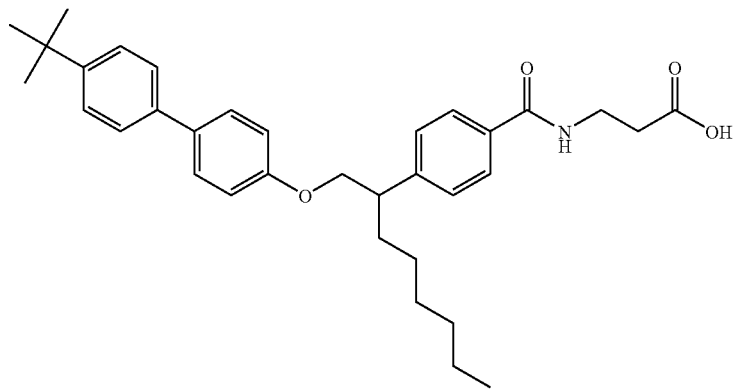 |
| X10 | 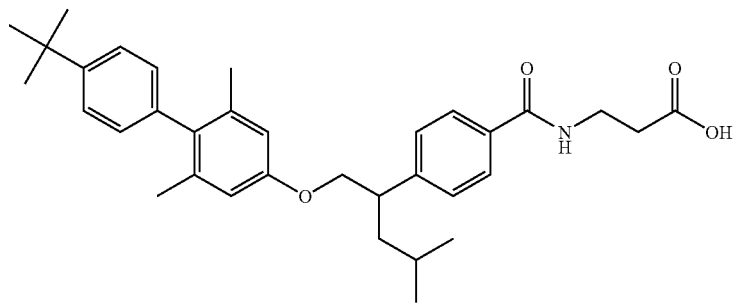 |
| X11 | 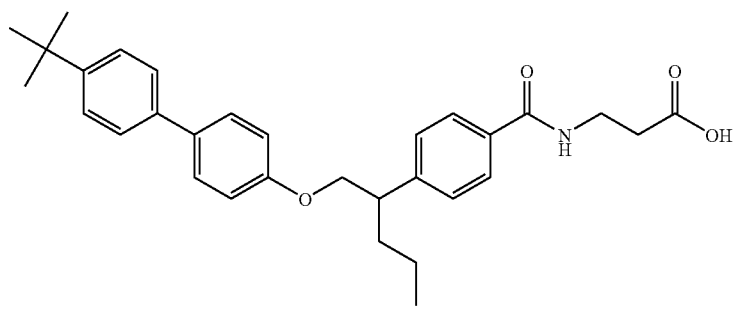 |

-continued

| Formula Number | Structure |
|---|---|
| X12 | 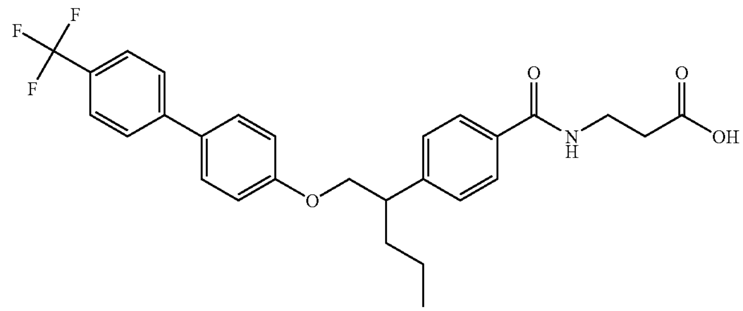 |
| X13 | 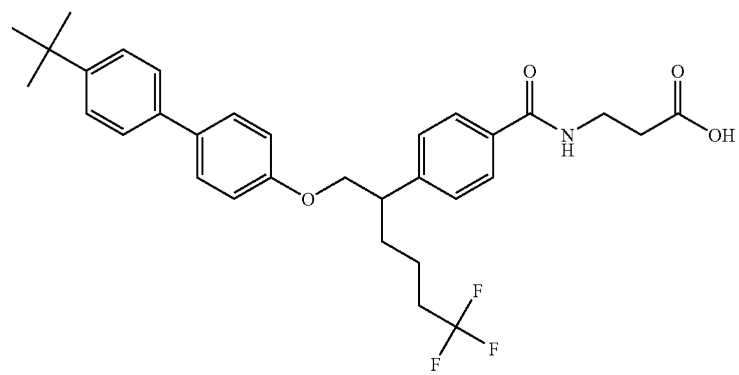 |
| X14 | 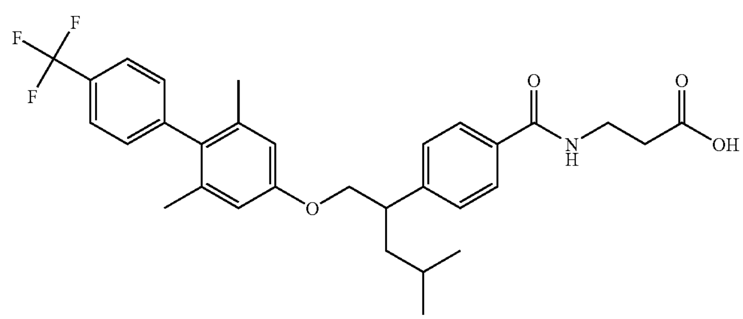 |
| X19 | 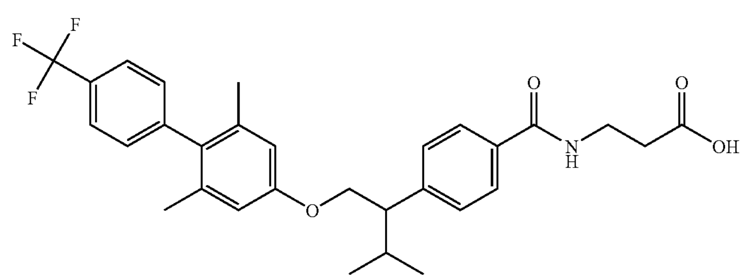 |
| X20 | 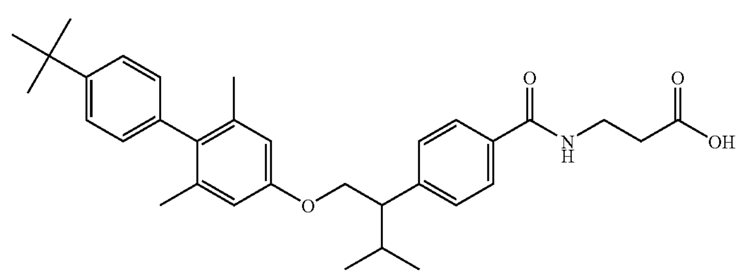 |

| Formula Number | Structure |
|---|---|
| X21 | 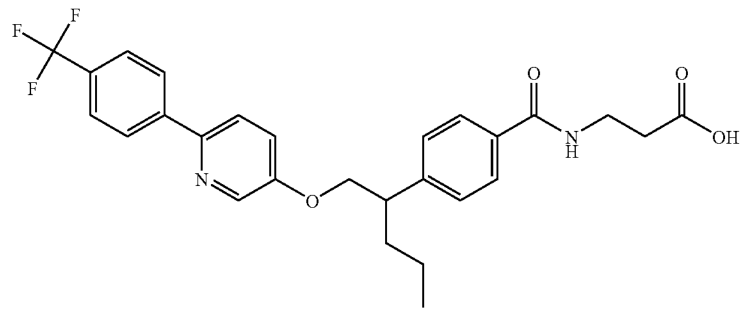 |
| X22 | | or a pharmaceutically acceptable salt thereof.

7. A compound of claim 1 selected from the group consisting of:
- racemic 3-{4-[1-(4'-Trifluoromethyl-biphenyl-4-yloxymethyl)-heptyl]-benzoylamino}-propionic acid;
- racemic 3-{4-[1-(4'-tert-Butyl-biphenyl-4-yloxymethyl)-heptyl]-benzoylamino}-propionic acid;
- racemic 3-{4-[1-(4'-tert-Butyl-2,6-dimethyl-biphenyl-4-yloxymethyl)-3-methyl-butyl]-benzoylamino}-propionic acid;
- racemic 3-{4-[1-(4'-tert-Butyl-biphenyl-4-yloxymethyl)-butyl]-benzoylamino}-propionic acid;
- racemic 3-{4-[1-(4'-Trifluoromethyl-biphenyl-4-yloxymethyl)-butyl]-benzoylamino}-propionic acid;
- racemic 3-{4-[1-(4'-tert-Butyl-biphenyl-4-yloxymethyl)-5,5,5-trifluoro-pentyl]-benzoylamino}-propionic acid;
- racemic 3-{4-[1-(2,6-Dimethyl-4'-trifluoromethyl-biphenyl-4-yloxymethyl)-3-methyl-butyl]-benzoylamino}-propionic acid;
- 3-{4-[1-(4'-Trifluoromethyl-biphenyl-4-yloxymethyl)-heptyl]-benzoylamino}-propionic acid, isomer 1;
- 3-{4-[1-(4'-Trifluoromethyl-biphenyl-4-yloxymethyl)-heptyl]-benzoylamino}-propionic acid, isomer 2;
- 3-{4-[1-(4'-tert-Butyl-2,6-dimethyl-biphenyl-4-yloxymethyl)-3-methyl-butyl]-benzoylamino}-propionic acid, isomer 1;
- 3-{4-[1-(4'-tert-Butyl-2,6-dimethyl-biphenyl-4-yloxymethyl)-3-methyl-butyl]-benzoylamino}-propionic acid isomer 2;
- 3-{4-[1-(2,6-Dimethyl-4'-trifluoromethyl-biphenyl-4-yloxymethyl)-3-methyl-butyl]-benzoylamino}-propionic acid, isomer 1;
- 3-{4-[1-(2,6-Dimethyl-4'-trifluoromethyl-biphenyl-4-yloxymethyl)-3-methyl-butyl]-benzoylamino}-propionic acid, isomer 2;
- racemic 3-{4-[1-(2,6-Dimethyl-4'-trifluoromethyl-biphenyl-4-yloxymethyl)-2-methyl-propyl]-benzoylamino}-propionic acid;
- racemic 3-{4-[1-(4'-tert-Butyl-2,6-dimethyl-biphenyl-4-yloxymethyl)-2-methyl-propyl]-benzoylamino}-propionic acid;
- racemic 3-(4-{1-[6-(4-Trifluoromethyl-phenyl)-pyridin-3-yloxymethyl]-butyl}-benzoylamino)-propionic acid;
- racemic 3-{4-[1-(2,6-Dimethyl-4'-trifluoromethyl-biphenyl-4-yloxymethyl)-4,4,4-trifluoro-butyl]-benzoylamino}-propionic acid;
- 3-{4-[1-(2,6-Dimethyl-4'-trifluoromethyl-biphenyl-4-yloxymethyl)-2-methyl-propyl]-benzoylamino}-propionic acid isomer 1;
- 3-{4-[1-(2,6-Dimethyl-4'-trifluoromethyl-biphenyl-4-yloxymethyl)-2-methyl-propyl]-benzoylamino}-propionic acid, isomer 2;
- 3-{4-[1-(4'-tert-Butyl-2,6-dimethyl-biphenyl-4-yloxymethyl)-2-methyl-propyl]-benzoylamino}-propionic acid, isomer 1;
- 33-{4-[1-(4'-tert-Butyl-2,6-dimethyl-biphenyl-4-yloxymethyl)-2-methyl-propyl]-benzoylamino}-propionic acid, isomer 2;
- 3-{4-[1-(2,6-Dimethyl-4'-trifluoromethyl-biphenyl-4-yloxymethyl)-4,4,4-trifluoro-butyl]-benzoylamino}-propionic acid, isomer 1; and
- 3-{4-[1-(2,6-Dimethyl-4'-trifluoromethyl-biphenyl-4-yloxymethyl)-4,4,4-trifluoro-butyl]-benzoylamino}-propionic acid, isomer 2;

wherein isomer 1 is the first isomer eluted in a chiral separation, and isomer 2 is the second isomer eluted in a chiral separation; or a pharmaceutically acceptable salt thereof.

8. A pharmaceutical composition which comprises a compound or salt of claim 7 and a pharmaceutically acceptable carrier.

9. A method for alleviating Type 2 Diabetes which comprises administering to a mammal in need of such alleviation an effective amount of a compound of claim 7.

10. A method for alleviating Type 2 Diabetes which comprises administering to a mammal in need of such alleviation an effective amount of a pharmaceutical composition which comprises a compound or salt of claim 7 and a pharmaceutically acceptable carrier.

* * * * *